US008824762B2

(12) United States Patent
Rivaz et al.

(10) Patent No.: US 8,824,762 B2
(45) Date of Patent: Sep. 2, 2014

(54) METHOD AND SYSTEM FOR PROCESSING ULTRASOUND DATA

(75) Inventors: Hassan Rivaz, Baltimore, MD (US); Gregory Hager, Baltimore, MD (US); Emad M. Boctor, Baltimore, MD (US); Ioana Fleming, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 312 days.

(21) Appl. No.: 13/279,970

(22) Filed: Oct. 24, 2011

(65) Prior Publication Data

US 2012/0128223 A1 May 24, 2012

Related U.S. Application Data

(60) Provisional application No. 61/405,890, filed on Oct. 22, 2010.

(51) Int. Cl.
| G06K 9/00 | (2006.01) |
| G06K 9/62 | (2006.01) |
| A61B 8/00 | (2006.01) |
| A61B 8/08 | (2006.01) |
| G06T 7/00 | (2006.01) |

(52) U.S. Cl.
CPC .............. *A61B 8/485* (2013.01); *G06K 9/6206* (2013.01); *A61B 8/587* (2013.01); *A61B 8/5269* (2013.01); *G06T 2207/10132* (2013.01); *G06T 2207/30004* (2013.01); *G06T 7/0028* (2013.01); *A61B 8/5207* (2013.01)
USPC .......................................................... 382/131

(58) Field of Classification Search
None
See application file for complete search history.

(56) References Cited

U.S. PATENT DOCUMENTS

| 7,386,163 | B2* | 6/2008 | Sabe et al. ..................... 382/153 |
| 8,155,405 | B2* | 4/2012 | Unal et al. ..................... 382/128 |
| 8,559,685 | B2* | 10/2013 | Rivaz et al. ................... 382/128 |
| 2002/0120195 | A1* | 8/2002 | Hossack et al. ............... 600/443 |
| 2007/0270687 | A1* | 11/2007 | Gardi et al. ................... 600/425 |
| 2008/0260221 | A1* | 10/2008 | Unal et al. ..................... 382/128 |
| 2008/0292194 | A1* | 11/2008 | Schmidt et al. ............... 382/217 |
| 2008/0306384 | A1* | 12/2008 | Boctor et al. .................. 600/443 |
| 2011/0050853 | A1* | 3/2011 | Zhang et al. ..................... 348/44 |
| 2012/0004539 | A1* | 1/2012 | Gardi et al. ................... 600/424 |

OTHER PUBLICATIONS

Amini et al., "Using dynamic programming for solving variational problems in vision," *IEEE Trans. Pattern Anal. Mach. 'well.*, vol. 12. No. 9. pp. 855-867. Sep. 1990.

(Continued)

*Primary Examiner* — Nancy Bitar
(74) *Attorney, Agent, or Firm* — Venable LLP; Henry J. Daley; George L. Howarah

(57) ABSTRACT

A method of processing ultrasound data includes receiving ultrasound data for a first ultrasound image, the first ultrasound image being represented as a first set of discrete pixels corresponding to positions of a region of interest; receiving ultrasound data for a second ultrasound image, the second ultrasound image being represented as a second set of discrete pixels corresponding to positions of the region of interest; generating a displacement map by minimizing a cost function using a dynamic programming procedure that identifies each of the first set of discrete pixels with a corresponding one of the second set of discrete pixels; refining the displacement map to obtain intermediate displacement values corresponding to positions between the discrete pixels based on minimizing a local approximation to the cost function; and calculating a physical property of the region of interest based on the displacement map.

24 Claims, 24 Drawing Sheets

(56) References Cited

OTHER PUBLICATIONS

Baker et al., "Lucas-kanade 20 years on: A unifying framework," Int. J. Comput. Vis., vol. 56. No. 3, pp. 221-255. Feb. 2004.
Barbone et al., "Quantitative elasticity imaging: What can and cannot be inferred from strain images." Phys. Med. Biol., vol. 47. pp. 2147-2164, Jun. 2002.
Bohs et al., "A novel method for angle independent ultrasonic imaging of blood flow and tissue motion." IEEE Trans. Ultrason. Ferroelectr. Freq. Control, vol. 38, No. 3, pp. 280-286, Mar. 1991.
Brusseau et al., "2-D locally regularized tissue strain estimation from radio-frequency ultrasound images, Theoretical developments and results on experimental data," IEEE Trans. Med. Imag,, vol. 27, No. 2, pp. 145-160. Feb. 2008.
Chaturvedi et al., "2-d companding for noise, reduction in strain imaging," IEEE Trans. Ultrason. Ferroeleetr, Freq. Control, vol. 45, No. 1, pp. 179-191. Jan. 1998.
Chen et al., "A quality-guided displacement tracking algorithm for ultrasonic elasticity imaging," Med. Thing. Anal., vol. 13, No. 2, pp. 286-296. Apr. 2009.
Chen et al., "Lateral speckle tracking using synthetic lateral phase," IEEE Trans. Ultrason. Ferroelectr. Freq. Control, vol. 51, No. 5, pp. 540-550, May 2004.
Doyley et al., "A freehand elastographic imaging approach for clinical breast imaging: System development and performance evaluation." Ultrasound Med. Biol.. vol. 27, pp. 1347-1357,2001.
Doyley, et al., "Performance analysis of steady-state harmoic elastography," Phys. Med. Biol., vol. 52, No., 10, pp. 2657-2674, May 2007.
Dugad et al., "Video denoising by combining Kalman and Wiener estimates." in Int. Conf. Image Process. ICIP, 1999. vol. 4, pp. 152-156.
Ebbini, "Phase-cupled two-dimensional speckle tracking algorithm," IEEE Trans. Ultrason. Ferroelectr. Freq. Control, vol. 53, No. 5, pp. 972-990, May 2006.
Gao et al., "Imaging of the elastic properties of tissue-A review," Ultrasound Med. Biol., vol. 22. No. 8, pp. 959-977. Aug. 1996.
Greenleaf, et al., "Selected methods for imaging elastic properties of biological tissues," Annu. Rev. Biomed., vol. 5, pp. 57-78. Apr. 2003.
Hager, et al., "Efficient region tracking with parametric models of geometry and illumination," IEEE Trans, Pattern Anal. Mach. Intell., vol. 20, No. 10, pp. 1025-1039, Oct. 1998.
Hall et al., "In vivo real-time freehand palpation imaging," Ultrasound Med. Biol., vol. 29, pp. 427-435, Mar. 2003.
Hasegawa et al., "Improving accuracy in estimation of artery wall displacement by referring to center frequency of RF echo . " IEEE Trans. Ultrason, Ferroelectr. Freq. Control. vol. 53. No. 1. pp. 52-63, Jan. 1999.
Hiltawsky et al., "Freehand ultrasound elastography of breast lesions: Clinical results," Ultrasound Med. Biol., vol. 27, pp. 1461-1469, Nov. 2001.
Holland et al., "Robust regression using iteratively reweighted least squares" Commun. Statist, Theory Methods, vol. A6, pp. 813-827,1977.
Insana et al., "Maximum-liklihood approach to strain imaging using ultrasound," IEEE Trans. Ultrason. Ferroelectr. Freq. Control, vol. 107, No. 3, pp. 1421-1434, 2000.
Jensen, "Field: A program for simulating ultrasound systems:" Med. Biol. Eng. Comput., vol. 34. pp. 351-353,1996.
Jiang et al., "Ultrasound-based relative elastic modulus imaging for visualizing thermal ablation zones in a porcine model," Phys. Med. Biol., vol. 55, pp. 2281-2306, 2010.
Jiang et al., "Young modulus reconstruction for radio frequency ablation electrode-induced displacement fields: A feasibility study," IEEE Trans. Med. Imag., vol. 28, pp. 1325-1334, Aug. 2009.
Konofagou et al., "A new elastographic method for estimation and imaging of lateral displacements, lateral strains, corrected axial strains and Poisson's ratios in tissues." Ultrasound Med BioL, vol. 24. No. 8. pp. 1183-1199,1998.

Konofagou et al., "Myocardial e las tography—A feasibility study in vivo," Ultrasound Med. Biol., vol. 28. No. 4. pp. 475-482, Apr. 2002.
Krouskop et al., "The elastic moduli of breast and prostate tissues under compression," Ultrason. Imag., vol. 20, pp. 260-274,1998.
Lindop et al., "3D elastography using freehand ultrasound?" Ultrasound Med. Biol., vol. 32, pp. 529-545. Apr. 2006,.
Lindop et al., "Phase-based ultrasonic deformation estimation." IEEE Trans. Ultrason. Ferroelectr. Freq. Control, vol. 55, No, 1, pp. 94-111,2008.
Liu et al., "Linear approach to axial resolution in elasticity imaging," IEEE Trans. Ultrason. Ferroelectr. Freq. Contra vol. 51. No. 6, pp. 716-725, Jun. 2004.
Lorenz et al., "A new system for the acquisition of ultrasonic multicompression strain images of the human prostate in vivo," IEEE Trans. Ultrason, Ferroelecto. Freq. Control, vol. 46, No. 9, pp. 1147-1154. Sep. 1999.
Lubinski et al., "Lateral displacement estimation using tissue incompressibility," IEEE Trans. Ultrason. Ferroelectr. Freq. Control. vol. 43. No. 2, pp. 247-255, Mar. 1996.
Lyshchik et al., "Thyroid gland tumor diagnosis at US elastography," Radiology,. vol. 237. No. 1, pp. 202-211, Aug. 2005.
Maurice et al., "Lagrangiiin speckle model and tissue-motion estimation theory," IEEE Trans. Med. knag., vol. 18. No. 7. pp. 593-603. Jul. 1999.
Maurice et al., "Noninvasive vascular elastography: Theoretical framework," IEEE Trans. Med. Intag.. vol. 23, No. 2, pp. 164-180, Feb. 2004.
Miga, "A new approach to elastography using mutual information and finite elements," Phys. Med. Biol., vol. 48, pp. 467-480, 2003.
O'Donnell et al., "Internal displacement and strain imaging using ultrasonic speckle tracking." IEEE Trans. Ultrason, Ferroelectr. Freq. Control, vol. 41, No. 3, pp. 314-325, Mar. 1994.
Ophir J, Alam SK, Garra B, et al. Elastography: ultrasonic estimation and imaging of the elastic properties of tissues Proc Inst Mech Eng H 1999;213:203-233.
Padgett et al., "Assessment of the effects of pixel loss on image quality in direct digital radiography." Phys, Med. Biol., vol. 49. No. 6, pp. 977-986, Mar. 2004.
Parker et al., "A unified view of imaging the elastic properties of tissue," J. Acoust. Soc. Amer., vol. 117, pp. 2705-2712, May 2005.
Pellot-Barakat et al., "Ultrasound elastography based on multiscale estimations of regularized displacement fields," IEEE Trans. Med. Lag., vol. 23, No. 2. pp. 153-163. Feb. 2004.
Pesavento et al., "A time efficient and accurate strain estimation concept for ultrasonic elastography using iterative phase zero estimation." IEEE Trans. Ultrason. Ferroelectr. Freq. Control, vol. 46, pp. 1057-1067, Sep. 1999.
Rao et al., "Normal and shear strain estimation using beam steering on Linear-array transducers," Ultrasound Med. Biol., vol. 33, No. 1, pp. 57-66, Jan. 2007.
Rivaz et al., "Ablation monitoring with elastography: 2d in-vivo and 3d ex-vivo studies," in Med. Image Comput. Comput. Assisi. inletvent. MICCAI, New York, Sep. 2008, pp. 458-466.
Rivaz et al., "Tracked regularized ultrasound elastography for targeting breast radiotherapy." in Med. Image Comput. Computer Assisi. Intermit. MICCA. London, U.K.. Sep. 2009, pp. 507-515.
Rivaz et al., "Ultrasound speckle detection using low order moments," in IEEE Int. Ultrason. Symp., Oct. 2006. pp. 2092-2095.
Rivaz, et al., "Ultrasound elastography: A dynamic programming approach." IEEE Trans. Med, Imag., vial, 27, No. 10. pp. 1373-1377. Oct. 2008.
Sandrin, et al., "Shear modulus imaging with 2-D transient elastography," IEEE Trans. Ultrason. Ferroelectr. Freq. Control, vol. 49, No. 4. pp. 426-4-35, Apr. 2002.
Shum et al., "Construction of panoramic mosaics with global and local alignment," Int. J. Comput. Vis., vol. 36, No. 2, pp. 101-130, 2000.
Sumi et al., "Regularization for ultrasonic measurements of tissue displacement vector and strain tensor," IEEE Trans. Ultrason, Ferroelectr. Freq. Comm, vol. 55, No. 4. pp. 787-799, Apr. 2008.

(56) References Cited

OTHER PUBLICATIONS

Sumi, "Displacement vector measurement using instantaneous ultrasound signal phase-Multidimensional autocorrelation and Doppler methods," *IEEE Trans. Ultrason, Ferroelectr. Freq. Control*, vol. 55, No. 1, pp. 24-43, Jan. 2008.

Sumi, "Reconstructions of shear modulus, Poisson's ratio, and density using approximate mean normal stress lambda epsilon alpha alpha as unknown," *IEEE Trans, Ultrason. Ferroelectr. Freq. Control*, vol. 53, No. 12_pp. 2416-2434. Dec. 2006.

Sumi, "Regularization of tissue shear modulus reconstruction using strain variance," *IEEE Trans, Ultrason. Ferroelectr. Freq. Control*, vol. 55. No. 2.. pp. 297-307, Feb. 2008.

Sumi. "Usefulness of ultrasonic strain measurement-based shear modulus reconstruction for diagnosis and thermal treatment," *IEEE Trans. Ultrason. Ferroeleetr Freq. Control*, vol. 52, No. 10, pp. 1670-1689, Oct. 2005.

Tarter et al., Ultrafast compound imaging for 2-d motion vector estimation: Application to transient elastography, *IEEE Trans. Ultrason. Ferroelectr. Freq. Control*. vol. 49, No. 10, pp. 1363-1374, Oct. 2002.

Treece et al., "Uniform precision ultrasound strain imaging," *IEEE Trans. Ultrason. Ferroelectr. Freq. Control*, vol. 56. No. 11, pp. 2420-2436, Nov. 2009.

Turgay, et al., "Identifying the mechanical properties of tissue by ultrasound strain imaging," *Ultrasound Med. Biol..* vol. 32, No. 2. pp. 221-2'35, Feb. 2006.

Varghese et al., "Elastography imaging of thermal lesion in the liver following radio frequency ablation: Preliminary results:" *Ultrasound Med. Biol..* vol. 28, No. 11. pp. 1467-1473, 2002.

Viola et al., "A comparison of the performance of time-delay estimators in medical ultrasound." *IEEE Trans. Ultrason. Ferroelectr. Freq. Control*, vol. 50, No. 4, pp. 392-401, Apr. 2003.

Wagner et al. "Statistics of speckle in ultrasound B-Scans," *IEEE Trans, Sonics Ultrasonics*, vol. 17, No. 3, pp. 251-268, May 1983.

Walker et al., "A fundamental limit on delay estimation using partially correlated speckle signals." *IEEE Trans. Ultrason. Ferroelectr. Freq. Control*, vol. 42, No. 2, pp. 301-308, Mar. 1995.

Welch et al., An introduction to the Kalman filter Univ. North Carolina. Chapel Hill, TR 95-041, 1995.

Yamakawa et al., "High-speed freehand tissue elasticity imaging for breast diagnosis,"*Jpn. J. App. Phys.*, vol. 42, No. 511. pp. 3265-3270. May 2003.

Yeung et al., "Multilevel and motion model-based ultrasonic speckle tracking algorithms," *Ultrasound Med. Biol.*, vol. 24. pp. 427-4-41, Mar. 1998.

* cited by examiner

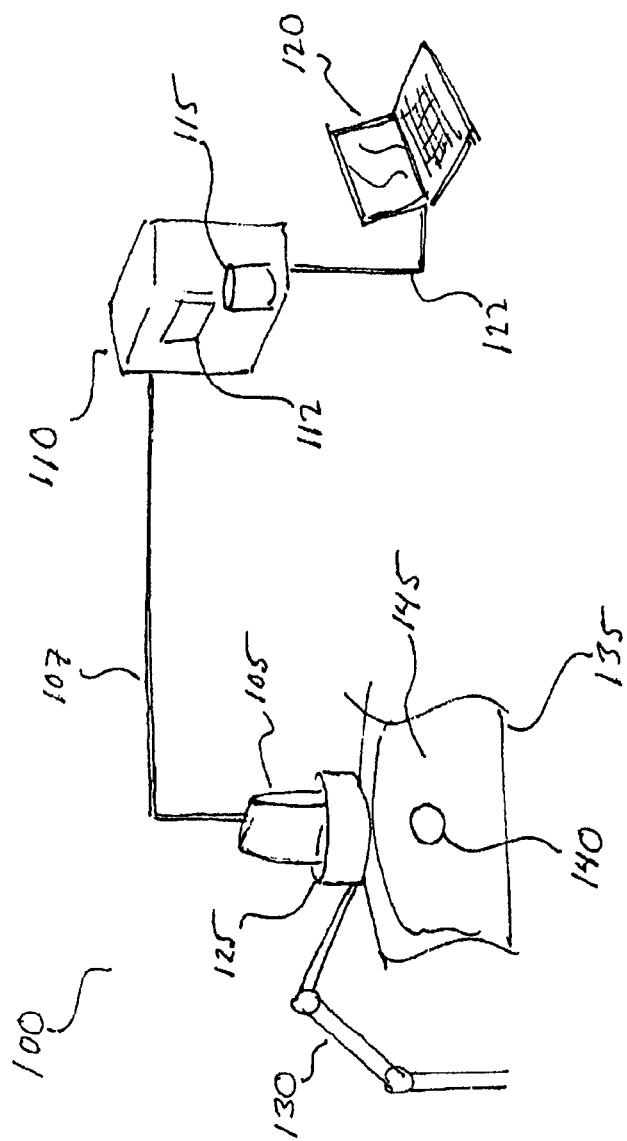

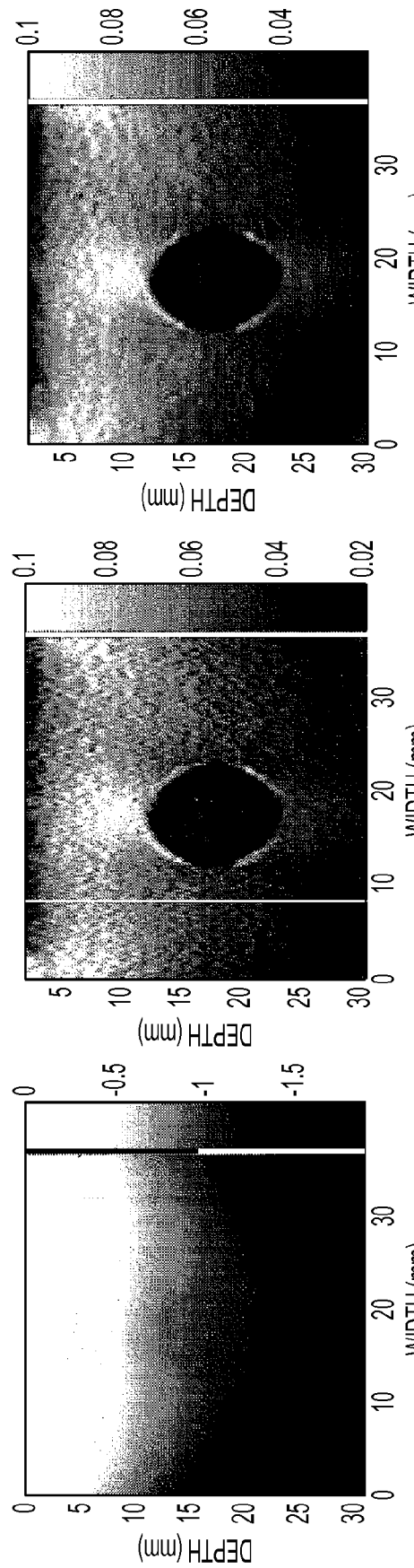

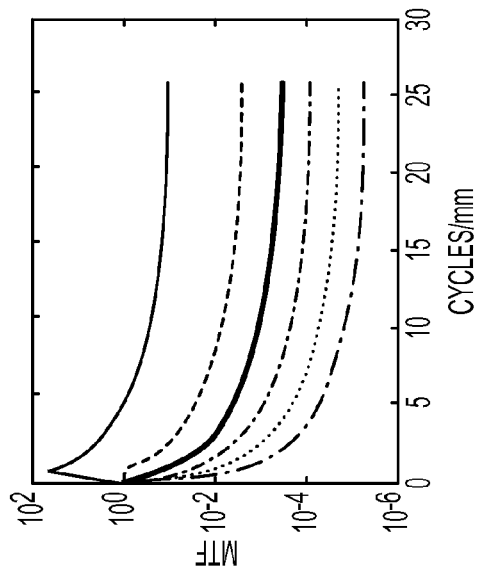
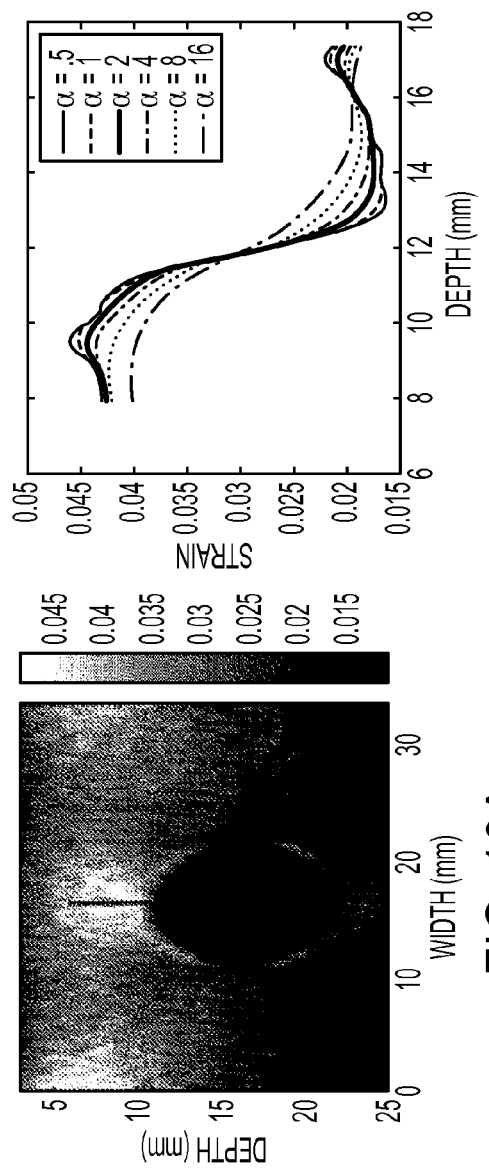
FIG. 10C
FIG. 10B
FIG. 10A

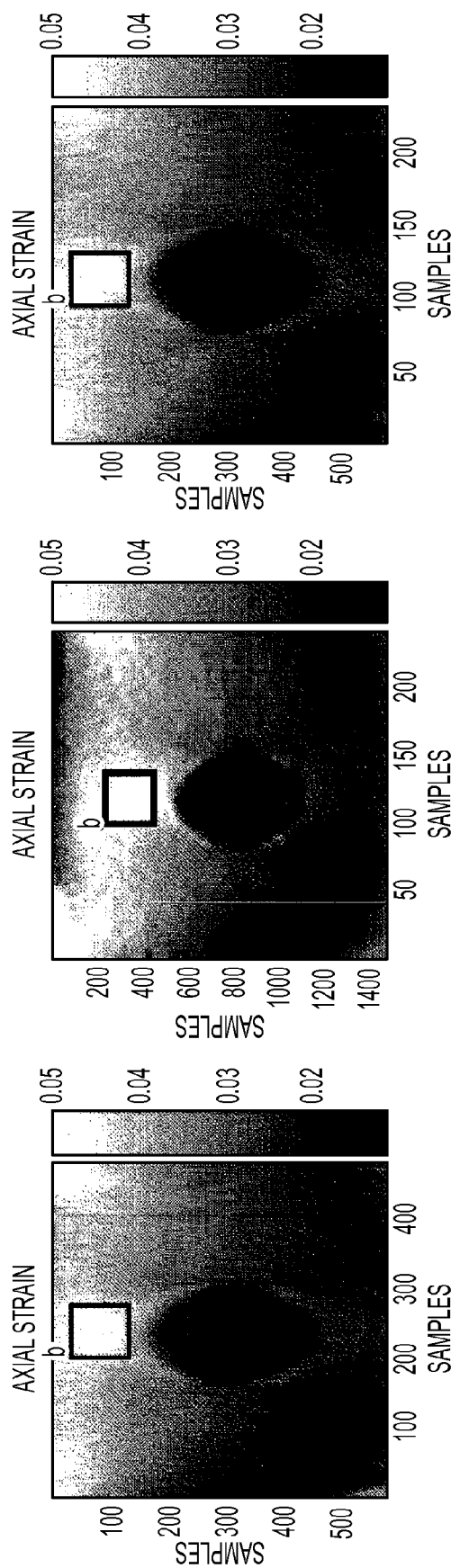

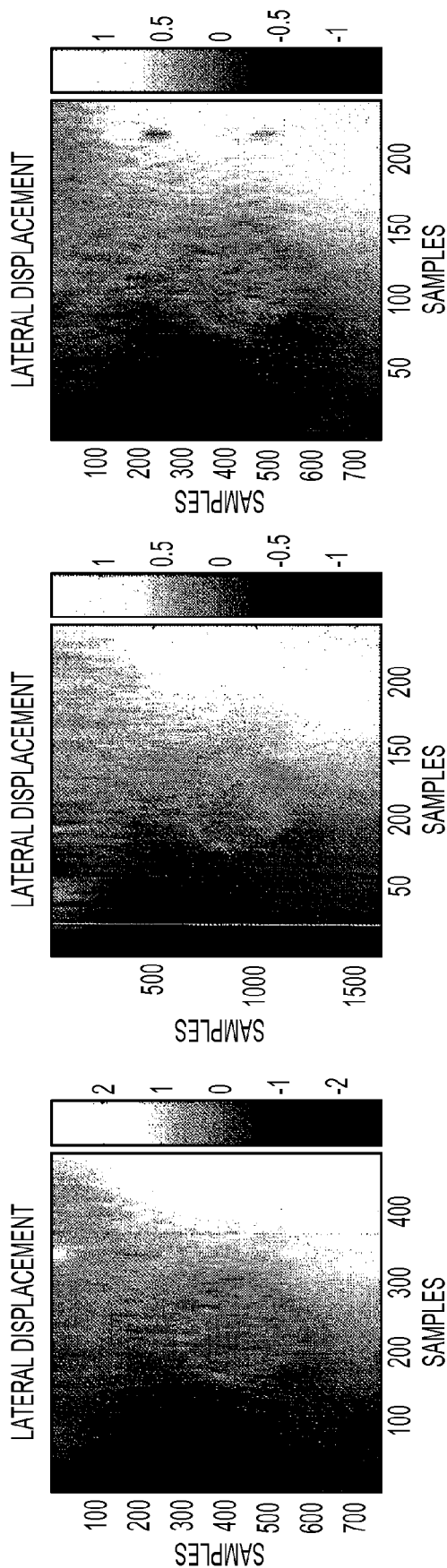

METHOD AND SYSTEM FOR PROCESSING ULTRASOUND DATA

CROSS-REFERENCE OF RELATED APPLICATION

This application claims priority to U.S. Provisional Application No. 61/405,890 filed Oct. 22, 2010, the entire contents of which are hereby incorporated by reference.

This invention was made with government support under W81XWH-09-1-0060 awarded by ARMY/MRMC, U.S. Army Medical Department, Medical Research and Materiel Command. The government has certain rights in the invention.

BACKGROUND

1. Field of Invention

The field of the currently claimed embodiments of this invention relates to systems and methods for processing ultrasound data, and more particularly to systems and methods for processing ultrasound data using dynamic programming procedures.

2. Discussion of Related Art

Ultrasound imaging is commonly used in detecting and targeting tumors, isolating organ structures, and monitoring invasive surgical procedures. One example of an intraoperative application of ultrasound involves its use in treating tumors. Such treatments include Electron Beam Radiation Therapy (EBRT) and hepatic tumor thermal ablation. A common challenge to these procedures is to accurately image the tumor so that the tumor can be treated most effectively while minimizing damage to the surrounding tissue. A further challenge encountered in such tumor therapies involves the ability to assess the state of the surrounding tissue after treatment or between treatments.

Conventional brightness (or B-mode) ultrasound has been used for intraoperative target imaging during thermal ablation procedures. However, B-mode ultrasound typically reveals only hyperechoic (i.e., brighter ultrasound signature) areas that result from microbubbles and outgassing from the ablated tissue. The tumor may be isoechoic, meaning that its brightness in ultrasound imagery is substantially indistinguishable from that of the surrounding tissue. In such cases, ablation effectiveness is estimated by the ultrasound-determined position of the ablation probe, and not by imagery of the tumor or surrounding tissue.

Ultrasound elasticity imaging has emerged as an effective technique to mitigate the disadvantages of B-mode ultrasound. Ultrasound elasticity imaging exploits the differences in mechanical properties of the tumor from those of the surrounding tissue medium. By imaging the deformation of the tissue in response to pressure exerted by the ultrasound probe, the contour of the tumor may be extracted from the surrounding tissue. In doing so, the ultrasound system generally tracks the deformation (or strain) of the tissue by tracking the motion of "speckle," or coherent scattering features within the tissue.

Although an improvement over B-mode ultrasound, related art ultrasound elasticity imaging has limitations. First, related art image processing techniques result in artifacts and noise that degrade the quality of the image, and thus may impede effective target imaging. Second, related art image processing techniques are generally computationally expensive, which often results in significant lag times in image display. The artifacts and noise in related art ultrasound elasticity imagery generally results from speckle decorrelation due to speckle out-of-plane motion, and shadowing.

Another problem regarding related art ultrasound elasticity imaging is that the technician may easily apply too much pressure to the tissue surrounding the tumor. This exacerbates the problem of out-of-plane motion, because the surrounding tissue spreads out of the path (and thus out of the field of view) of the ultrasound probe. Further, applying too much pressure on the surrounding tissue may dislocate the tumor and temporarily alter its shape. Once the pressure is released, the tumor may return to its original location and shape. As such, the location and shape of the imaged tumor (when pressure is applied) may be different from the location and shape of the tumor in its "rest" state. The resulting inaccuracy in target imaging may result in inaccurate delivery of heat or radiation during treatment. Additionally, in the case of multiple treatments, because each technician may apply differing degrees of force, dislocation and distortion of the tumor may further degrade the precision of the determined location and size of the tumor.

Accordingly, there remains a need for improved systems and methods for processing ultrasound data.

SUMMARY

A method of processing ultrasound data according to some embodiments of the current invention includes receiving ultrasound data for a first ultrasound image, the first ultrasound image being represented as a first set of discrete pixels corresponding to positions of a region of interest; receiving ultrasound data for a second ultrasound image, the second ultrasound image being represented as a second set of discrete pixels corresponding to positions of the region of interest; generating a displacement map by minimizing a cost function using a dynamic programming procedure that identifies each of the first set of discrete pixels with a corresponding one of the second set of discrete pixels; refining the displacement map to obtain intermediate displacement values corresponding to positions between the discrete pixels based on minimizing a local approximation to the cost function; and calculating a physical property of the region of interest based on the displacement map.

A computer readable medium according to some embodiments of the current invention includes software, which software when executed by a computer, causes the computer to receive ultrasound data for a first ultrasound image, the first ultrasound image being represented as a first set of discrete pixels corresponding to positions of a region of interest; receive ultrasound data for a second ultrasound image, the second ultrasound image being represented as a second set of discrete pixels corresponding to positions of the region of interest; generate a displacement map by minimizing a cost function using a dynamic programming procedure that identifies each of the first set of discrete pixels with a corresponding one of the second set of discrete pixels; refine the displacement map to obtain intermediate displacement values corresponding to positions between the discrete pixels based on minimizing a local approximation to the cost function; and calculate a physical property of the region of interest based on the displacement map.

An ultrasound system according to some embodiments of the current invention includes an ultrasound transducer configured to transmit and receive ultrasound signals, and a data processor arranged to communicate with the ultrasound transducer to receive ultrasound data from the ultrasound transducer. The data processor is configured to receive ultrasound data for a first ultrasound image, the first ultrasound image being represented as a first set of discrete pixels corresponding to positions of a region of interest; receive ultrasound data for a second ultrasound image, the second ultrasound image being represented as a second set of discrete pixels corresponding to positions of the region of interest; generate a displacement map by minimizing a cost function using a dynamic programming procedure that identifies each of the first set of discrete pixels with a corresponding one of the second set of discrete pixels; refine the displacement map to obtain intermediate displacement values corresponding to positions between the discrete pixels based on minimizing a local approximation to the cost function; and calculate a physical property of the region of interest based on the displacement map.

BRIEF DESCRIPTION OF THE DRAWINGS

Further objectives and advantages will become apparent from a consideration of the description, drawings, and examples.

FIG. 1B is a schematic illustration of an ultrasound system according to an embodiment of the current invention.

FIG. 2A: In $I_2$ the initial estimates (in black) are updated by the arrows (three components of $\Delta d$) to new estimates (in red) after an iteration of 2D AM. To find $\Delta d$ using (19), it is required to calculate image gradient at the off-grid initial estimate locations (in black) on $I_2$. FIG. 2B: Schematic plot of two RF-data $I_1$ and $I_2$, each sampled at three locations (black dots). The black dashed-dotted arrow shows $\Delta a$ of the sample on $I_1$ (ignoring the regularization term) which requires calculating the gradient on $I_2$ at an off-grid location. The blue dashed arrow shows $\Delta a$ of an off-grid sample on $I_2$ (ignoring the regularization term) which requires calculating the gradient on $I_1$ at an on-grid location. Ignoring second-order derivatives, the length of the two arrows is equal. FIG. 2A. Three samples on $I_1$ (left) and corresponding matches on $I_2$ (right). FIG. 2B. Inverse gradient estimation.

FIG. 9A-9F show phantom experimental results. The top row shows axial displacement and axial strains as labeled (KF in (9C) refers to Kalman filter). Average axial strain and maximum strain are approximately 6.6% and 11%. (9D) and (9E) show lateral displacement and lateral strain, respectively. (9F) shows residuals as the regularization weight varies. (9A) Axial displacement (mm). (9B) Axial strain. (9C) Axial strain with KF. (9D) Lateral displacement (mm). (9E) Lateral strain. (9F) Residuals.

FIGS. 10A-10C show phantom experimental results showing the resolution of the 2D AM. (10A) Strain image. The edge spread function is evaluated along the vertical line. (10B) The strain across the edge [vertical line in (10A)] for the five shown regularization values. (10C) The MTF calculated across the vertical line in (10A). Spatial resolution is defined as the spatial frequency when the value of MTF is 0.1. (10A) Axial strain. (10B) Strain profile. (10C) MTF.

FIGS. 11A-11I show results of the CIRS elastography phantom at 5% maximum strain at different axial and lateral sampling rates. The hard lesion is spherical and has a diameter of 1 cm. Downsampling is performed by simply skipping samples in the axial or (and) lateral directions. In (11C and 11F)), a downsampling ratio of 2 is applied in both axial and lateral directions. The lateral displacement is shown in number of samples in (11D)-(11F). (11H) and (11I) show the CNR between the target and background windows in the strain images as the axial or lateral downsampling rates change. The target and background windows are shown in the axial strain images (11A-(11C) and the lateral strain image (11G). In (11I), the lateral strain curve is not calculated for downsampling ratios of 6 and higher because the background window moves out of the image. The black dashed curve with the highest CNR is the strain obtained with the Kalman filter (KF). (11A) Axial downsamp. ratio=2. (11B) Lateral downsamp. ratio=2. (11C) Ax.-lat. downsamp. rat=2. (11D) Axial downsamp. ratio=2. (11E) Lateral downsamp. ratio=2. (11F) Ax.-lat. downsamp. rat=2. (11G) Lateral downsamp. ratio=2.

DETAILED DESCRIPTION

Figure 1A:
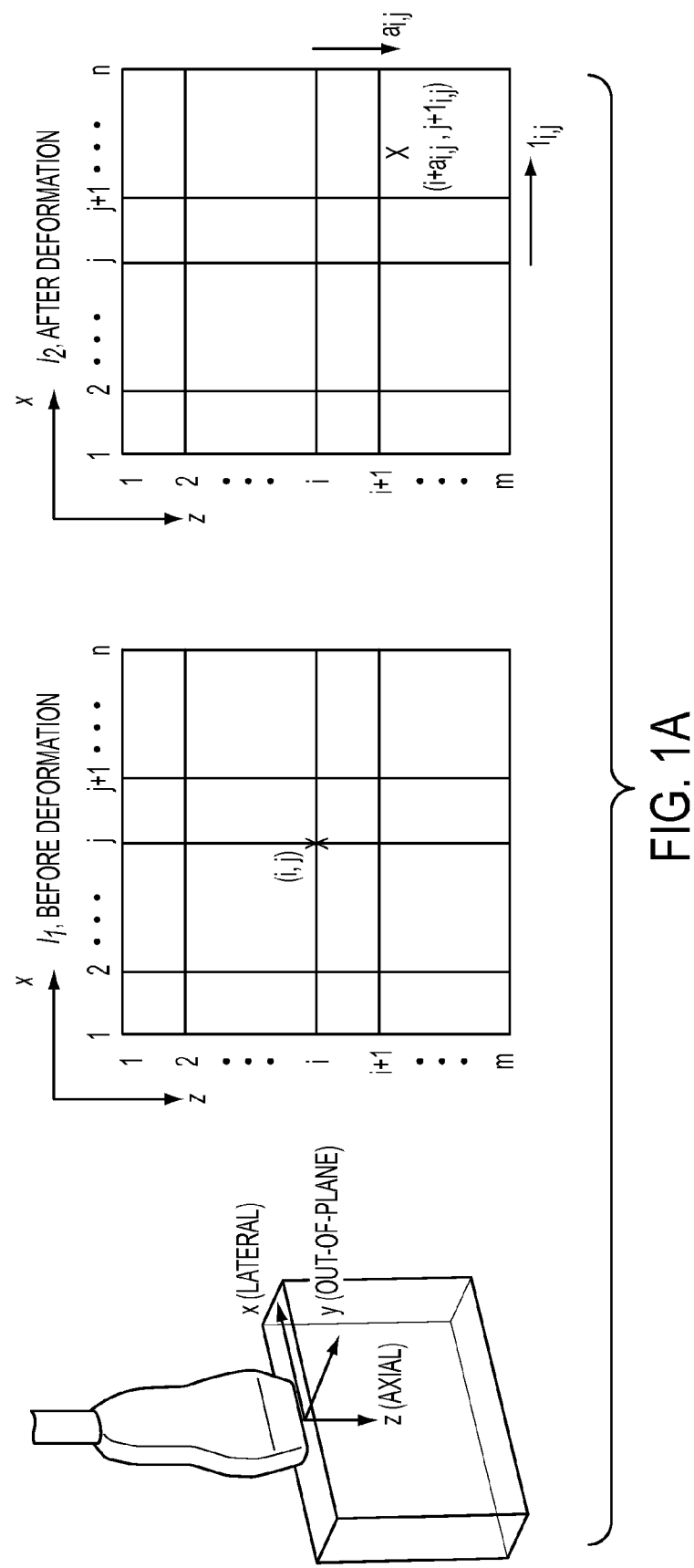
FIG. 1A is a schematic illustration to explain some concepts of methods of processing ultrasound data and ultrasound systems according to an embodiment of the current invention. Axial, lateral, and out-of-plane directions are shown. The coordinate system is attached to the ultrasound probe. The sample (i, j) marked by x moved by $(a_{i,j}, l_{i,j})$, $a_{i,j}$ and $l_{i,j}$ are, respectively, axial and lateral displacements and initially are integer in dynamic programming (DP).

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated. The references cited in square brackets are listed at the end of the specification.

Elastography involves imaging the mechanical properties of tissue and has numerous clinical applications. Among many variations of ultrasound elastography [1]-[4], some embodiments of the current invention focuses on real-time static elastography, a well-known technique that applies quasi-static compression of tissue and simultaneously images it with ultrasound. Within many techniques proposed for static elastography, some embodiments of the current invention are directed to freehand palpation elasticity imaging which involves deforming the tissue by simply pressing the ultrasound probe against it. It requires no extra hardware, provides ease of use and has attracted increasing interest in recent years [5]-[10]. Real-time elastography is of key importance in many diagnosis applications [11], [6], [12], [8], [13] and in guidance/monitoring of surgical operations [14]-[16].

Global and local decorrelation between the pre- and post-compression ultrasound images compromises the quality of the elasticity images. The main sources of global decorrelation in freehand palpation elastography are change of speckle appearance due to scatterer motion and out-of-plane motion of the probe (axial, lateral and out-of-plane directions are specified in FIG. 1A). Examples of local decorrelation are: 1) a decrease in the ultrasonic signal to noise ratio with depth, 2) low correlation close to arteries due to complex motion and inside blood vessels due to blood motion, 3) extremely low correlation in lesions that contain liquid due to the incoherent fluid motion [17], [8], and 4) out-of-plane motion of movable structures within the image [17].

Most elastography techniques estimate local displacements of tissue based on amplitude correlation [18], [2] or phase correlation of the radio-frequency (RF) echoes [19]-[21]. Assuming a stationary signal model for the RF data, the use of large correlation windows helps to reduce jitter errors (variance) for all motion field estimation techniques studied in [18] and [22]. This is intuitive as larger windows contain more information. However, in practice RF data is not stationary and, for large deformations, the decorrelation increases with window size. Therefore, in addition to reducing the spatial resolution [23], larger windows result in significant signal decorrelation [24], [23], [18]. Coarse-to-fine hierarchical search is used in [23] to combine the accuracy of large windows with the good spatial resolution of small window. However, the issue of signal decorrelation within the window remains unresolved in this approach and can cause the highest level of the hierarchical search to fail.

All of the aforementioned methods either do not calculate the lateral displacement or they just calculate an approximate integer lateral displacement. A two-dimensional (2D) displacement field is required to calculate the thermal expansion, lateral and shear strain fields [25] (i.e., reconstruct the strain tensor), Poisson's ratio and Young's modulus [26], [27]. The axial resolution of ultrasound is determined by the pulse length, and the lateral resolution is dictated by the center frequency of the excitation and the transducer pitch. Therefore, the lateral resolution is of order of magnitude lower than axial resolution. As a result, few 2D elastography techniques have been proposed to date. Initially, 2D motion estimation started in the field of blood flow estimation using speckle tracking [28]. Designed for blood flow estimation, these techniques are not immediately suitable for elastography which involves tissue deformation.

Attaching a coordinate system to the ultrasound probe as in FIG. 1A, z, x, and y in the ultrasound image are generally defined as axial, lateral and out-of-plane directions. Assume that the applied compression to the tissue is the Z direction, and attach a coordinate system X Y, Z to the applied force. Letting $d_Z$ and $d_N$ be the displacements in the Z and N directions where N⊥Z, axial and transverse strains are $\partial d_Z/\partial Z$ and $\partial d_N/\partial N$. In most experimental setups (including freehand palpation elastography), z and Z are parallel and N will be either lateral or out-of-plane, and therefore $d_N$ cannot be estimated accurately.

To calculate an accurate transverse strain, Z and z are perpendicular in [29] by applying the compression force perpendicular to the ultrasound imaging axis. Therefore, transverse strain is in the z direction of the ultrasound probe and hence can be measured with high accuracy. However, such an experimental setup is not possible in many medical applications. Beam steering has been used to solve this issue [30]. In freehand palpation elastography, beam steering causes z and Z to be unparallel, so that a component of the $d_X$ is in the z direction. The steering angle determines the angle between z and Z. Unfortunately, large steering angles are required to obtain accurate estimates of lateral strain, which is possible in phased arrays and not in linear arrays.

Lateral strains estimation is obtained in [31] by iteratively calculating axial strain, companding RF data and interpolating in the lateral direction. (We hereafter assume the applied force is in the z direction (i.e., Z and z are parallel) and therefore we use the term lateral strain instead of the term transverse strain.) In another work [32], tissue deformation is modeled by locally affine transformations to obtain both lateral and axial strains. Change of speckle appearance is taken into account by proposing a Lagrangian speckle model [33]. Although they provide high quality lateral strain, these techniques are computationally expensive and are not suitable for real-time implementation.

Axial strain is used in [34] to enhance the quality of lateral displacement estimation. Tissue is assumed to be incompressible and isotropic and therefore axial, lateral and out-of-plane strains should add to zero. However, many tissues cannot be considered incompressible. In fact, some research has even focused on imaging the ratio of the axial and lateral strain (i.e., the Poisson's ratio ν) [31].

While most previously mentioned methods use tissue motion continuity to confine the search range for the neighboring windows, the displacement of each window is calculated independently and hence is sensitive to signal decorrelation. Since data alone can be insufficient due to signal decorrelation, Pellot-Barakat et al. [35] proposed minimizing a regularized energy function that combines constraints of conservation of echo amplitude and displacement continuity. In another work [36], both signal shift and scale are found through minimization of a regularized cost function. The computation times of these methods are reported to be a few minutes and therefore they are not immediately suitable for real time elastography. In [37] and [38], few phase-based methods are regularized and strain and elasticity modulus images are obtained. The regularization term is the Laplacian (second derivative) of the motion field and is spatially variant based on the peak-value of the correlation coefficient. The regularization makes the method significantly more robust to signal decorrelation. However, it is still prone to decorrelation within each window especially for large strain rates. In a recent work [39], a displacement field is first calculated by minimizing phase differences in correlation windows [21]. The strain image is then estimated from the displacement field by optimizing a regularized cost function. The regularization assures smooth strain image calculation from the noisy displacement estimates.

Dynamic programming (DP) can be used to speed the optimization procedure [40], but it only gives integer displacements. (See also U.S. application Ser. No. 11/905501, U.S. Published App. No. 2008/0306384 A1, filed Oct. 1, 2007, the entire contents of which are incorporated herein by reference.) Subsample displacement estimation is possible [40], but it is computationally expensive, particularly if subsample accuracy is needed in both axial and lateral directions. Therefore, only axial subsample displacement is calculated [40]. In addition, a fixed regularization weight is applied throughout the image. To prevent regions with high local decorrelation from introducing errors in the displacement estimation one should use large weights for the regularization term, resulting in over-smoothing.

Some embodiments of the current invention are directed to two novel real-time elastography methods based on analytic minimization (AM) of cost functions that incorporate similarity of echo amplitudes and displacement continuity. Similar to DP, the first method gives subsample axial and integer lateral displacements. The second method gives subsample 2D displacement fields and 2D strain fields. The size of both displacement and strain fields is the same size as the RF-data (i.e., the methods are not window based and the displacement and strain fields are calculated for all individual samples of RF-data). An embodiment of the current invention provides a novel regularization term and demonstrates that it minimizes displacement underestimation caused by smoothness constraint. Another embodiment of the current invention introduces the use of robust statistics implemented via iterated reweighted least squares (IRLS) to treat uncorrelated ultrasound data as outliers. Another embodiment of the current invention introduces the use of Kalman filtering [41] for calculating strain images from the displacement fields. Simulation and experimental results according to some exemplar embodiments of the current invention are provided below. Also, an example of a clinical pilot study utilizing the system according to an embodiment of the current invention for monitoring thermal ablation in patients with liver tumors is also provided below.

An embodiment of the current invention is directed to a method of processing ultrasound data that includes receiving ultrasound data for a first ultrasound image and receiving ultrasound data for a second ultrasound image. The first ultrasound image is represented as a first set of discrete pixels corresponding to positions of a region of interest and the second ultrasound image is represented as a second set of discrete pixels corresponding to positions of the region of interest. The term "ultrasound data" is intended to broadly include ultrasound data in any form that can be processed for ultrasound imaging. For example, it can be radio frequency (RF) ultrasound data, or processed RF data. Processed ultrasound data can include, but is not limited to, ultrasound data that is mixed and filter to envelope detect, for example, to reduce from RF to video. Further filtering and processing can also be done. The term "pixel" is intended to broadly refer to a picture element that can include one-dimensional, two-dimension and/or three-dimensional pixels. Three-dimensional pixels are sometimes also referred to as voxels. Voxels are intended to be included within the definition of the term "pixel." For example, pixels can be discrete elements of A-mode, B-mode and/or C-mode ultrasound images.

The method of processing ultrasound data also includes generating a displacement map by minimizing a cost function using a dynamic programming procedure that identifies each of the first set of discrete pixels with a corresponding one of the second set of discrete pixels, refining the displacement map to obtain intermediate displacement values corresponding to positions between the discrete pixels based on minimizing a local approximation to the cost function, and calculating a physical property of said region of interest based on the displacement map.

The term "dynamic programming" refers to a method for solving complex problems by breaking them down into simpler sub-problems. It is applicable to problems exhibiting the properties of overlapping sub-problems, which are only slightly smaller and optimal substructure. When applicable, the method takes far less time than naive methods. In terms of mathematical optimization, dynamic programming usually refers to simplifying a decision by breaking it down into a sequence of decision steps over time. This is done by defining a sequence of value functions V1, V2, . . . Vn, with an argument y representing the state of the system at times i from 1 to n. The definition of Vn(y) is the value obtained in state y at the last time n. The values Vi at earlier times i=n-1,n-2, . . . , 2, 1 can be found by working backwards, using a recursive relationship called the Bellman equation. For i=2, . . . , n, Vi-1 at any state y is calculated from Vi by maximizing a simple function (usually the sum) of the gain from decision i-1 and the function Vi at the new state of the system if this decision is made. Since Vi has already been calculated for the needed states, the above operation yields Vi-1 for those states. Finally, V1 at the initial state of the system is the value of the optimal solution. The optimal values of the decision variables can be recovered, one by one, by tracking back the calculations already performed.

In some embodiments of the current invention, the minimizing of the local approximation of the cost function can be performed analytically to optimize the intermediate displacement values corresponding to positions within a continuous range between the discrete pixels. In some embodiments of the current invention, the receiving ultrasound data for the first ultrasound image can correspond to the region of interest being under a first compression state, the receiving ultrasound data for the second ultrasound image can correspond to the region of interest being under a second compression state, such that the calculating the physical property of the region of interest based on the displacement map is calculating a strain map. The term "compression state" is intended to include conditions in which positive or zero pressure is applied to the region of interest. Although less practical in some ultrasound applications, the term compression state can also include situations of negative compression, i.e., stretching. Therefore, a first compression state and a second compression state can refer to situations in which no pressure is applied, followed by applying a pressure. It can also include situations in which a first non-zero pressure is applied followed by a second non-zero pressure. The first and second non-zero pressures will typically be different values, but generally they could also be equal. In some embodiments of the current invention, the calculating the strain map can include Kalman filtering. In some embodiments of the current invention, the method can further include rendering an ultrasound image taking into account the strain map.

The broad concepts of the current invention are not limited to only rendering strain images. For example, in some embodiments of the current invention, the receiving ultrasound data for the first ultrasound image can correspond to the region of interest having a first temperature distribution, the receiving ultrasound data for the first ultrasound image can correspond to the region of interest having a second temperature distribution, and the calculating the physical property of the region of interest based on the displacement map is calculating a temperature map. The method of processing ultrasound data according to according to some embodiments of the current invention can further include rendering an ultrasound image taking into account the temperature map.

In some embodiments of the current invention, the cost function can be modified to reduce errors on the generating the displacement map due to portions of the region of interest moving out of an imaging plane of at least one of the first and second ultrasound images. In some embodiments of the current invention, the cost function can be modified to reduce errors on the generating the displacement map using an iterated reweighted least squares procedure to treat uncorrelated ultrasound data as outliers. The term "iterated reweighted least squares" (IRLS) refers to a method used to solve certain optimization problems. It solves objective functions of the form:

$$\operatorname{argmin}_r \Sigma \omega_i(r)(y_i - f_i(r))^2$$

by an iterative method. IRLS is used to find the maximum likelihood estimates of a generalized linear model, and in robust regression to find an M-estimator, as a way of mitigating the influence of outliers in an otherwise normally-distributed data set. For example, by minimizing the least absolute error rather than the least square error. One of the advantages of IRLS over linear and convex programming is that it can be used with Gauss-Newton and Levenberg-Marquardt numerical algorithms.

Some embodiments of the current invention are directed to a computer readable medium comprising software, which software when executed by a computer, causes the computer to receive ultrasound data for a first ultrasound image, the first ultrasound image being represented as a first set of discrete pixels corresponding to positions of a region of interest; receive ultrasound data for a second ultrasound image, the second ultrasound image being represented as a second set of discrete pixels corresponding to positions of the region of interest; generate a displacement map by minimizing a cost function using a dynamic programming procedure that identifies each of the first set of discrete pixels with a corresponding one of the second set of discrete pixels; refine the displacement map to obtain intermediate displacement values corresponding to positions between the discrete pixels based on minimizing a local approximation to the cost function; and calculate a physical property of the region of interest based on the displacement map. The software, according to some embodiments of the current invention, can be configured to perform the above-noted methods on the computer when executed.

FIG. 1B is a schematic illustration of an ultrasound system 100 according to some embodiments of the current invention. The ultrasound system 100 includes an ultrasound probe 105 adapted to communicate with a computer 110 over a signal cable 107. The computer 110 can be configured with a data processor 112 and a memory 115. The computer 100 can also have a user interface 120, which can be integrated into computer 120, or can be a separate computer that communicates with computer 110 over a network connection 122.

The ultrasound system 100 may also include an optional ultrasound probe mount 125, which may be connected to a mechanical arm 130. Mechanical arm 130, which is optional, may be a robotic arm that is controlled by computer 110, or a passive arm that serves to stabilize probe mount 125. In the latter case, ultrasound probe 105 and probe mount 125 may be moved (translated and/or rotated) manually by a technician.

Ultrasound probe 105 can be a commercially available ultrasound probe. Ultrasound probe 105, computer 110, and user interface 120 may be components of a commercially available ultrasound imaging system.

Computer 110 can be a single computer or can be multiple computers that can be co-located, or can be remotely located from each other and connected to each other over a network. Similarly, processor 112 can be a single computer processor or multiple processors, which can be distributed over multiple computers.

Memory 115 can include one or more electronic storage media (e.g., but not limited to, hard drive, flash drive, RAM, optical storage, etc.) that can be located within computer 110, or distributed over multiple computers. One skilled in the art will readily appreciate that many such variations to ultrasound system 100 are possible and within the scope of the current invention.

Memory 115 can be encoded with computer readable instructions and data (hereinafter "the software") for performing processes associated with embodiments of the current invention. If ultrasound probe 105, computer 110, and user interface 120 are parts of an integrated commercially available ultrasound imaging system, then the software according to some embodiments of the current invention can be installed and integrated into existing machine readable instructions and data that come bundled with the ultrasound imaging system.

FIG. 1B illustrates ultrasound probe 105 acoustically coupled to a patient's anatomy 135, which includes a tissue medium 145. Within tissue medium is an aberration 140. Aberration 140 may be any region or object within tissue medium 140 that has mechanical properties, such as Young's Modulus, that is different from that of surrounding tissue medium 145. Examples of aberration 140 include a tumor, a region of ablated tissue, a foreign object, a cavity resulting from a removed tumor, an organ—such as a prostate gland, and the like. Tissue medium 145 may include a liver, a breast, or any tissue region that surrounds aberration 140.

EXAMPLES

II. Methods

Assume that the tissue undergoes a deformation and let I1 and I2 be two images acquired from the tissue before and after the deformation. Letting $I_1$ and $I_2$ be of size m×n (FIG. 1), our goal is to find two matrices A and L where the (i, j)th component of $A(a_{i,j})$ and $L(l_{i,j})$ are the axial and lateral motion of the pixel (i, j) of $I_1$ (we are not calculating the out-of-plane motion). The axial and lateral strains are easily calculated by spatially differentiating A in the axial direction (resulting in $A_a$) and L in the lateral direction (resulting in $L_l$). The shear strains (not calculated in this work) can also be easily calculated by spatially differentiating A in the lateral direction (resulting in $A_l$) or L in the axial direction (resulting in $L_a$).

In this section, we first give a brief overview of a previous work (DP) that calculates integer values for A and L. We then propose 1D analytic minimization (AM) as a method that takes the integer displacement field from DP and refines the axial displacement component. We then introduce 2D analytic minimization (AM) that takes the integer displacement of a single RF-line from DP and gives the subsample axial and lateral displacement fields for the entire image. We conclude this section by presenting a technique for calculating smooth strain field from the displacement field using Kalman filtering.

A. Dynamic Programming (DP)

In order to present the general DP formulation, we consider a single column j (an RF-line) in $I_1$ (the image before deformation) in FIG. 1. Let m and n be the length of the RF-lines and the number of RF-lines in the images (FIG. 1). Let $a_i$ and $l_i$ denote the axial and lateral displacements of the ith sample of the RF-line in column j. In DP elastography [40], a regularized cost function is generated by adding the prior of displacement continuity (the regularization term) to an amplitude similarity term. The displacement continuity term for column j is $$R_j(a_i, l_i, a_{i-1}, l_{i-1}) = \alpha_a(a_i - a_{i-1})^2 + \alpha_l(l_i - l_{i-1})^2 \quad (1)$$

which forces the displacements of the sample i (i.e., $a_i$ and $l_i$) be similar to the displacements of the previous sample i−1 (i.e., $a_{i-1}$ and $l_{i-1}$). $\alpha_a$ and $\alpha_l$ are axial and lateral regularization weights respectively. We write $R_j(a_i, l_i, a_{i-1}, l_{i-1})$ to indicate the dependency of $a_i$ and $l_i$ on j. The regularized cost function for column j is then generated as following:

$$C_j(a_i, l_i, i) = [I_1(i, j) - I_2(i + a_i, j + l_i)]^2 + \min_{d_a, d_l} \left\{ \frac{C_j(d_a, d_l, i-1) + C_{j-1}(d_a, d_l, i)}{2} + R_j(a_i, l_i, d_a, d_l) \right\} \quad (2)$$

where $d_a$ and $d_l$ are temporary displacements in the axial and lateral directions that are varied to minimize the term in the bracket. After calculating $C_j$ for i=2...m, $C_j$ is minimized at i=m giving $a_m$ and $l_m$. The $a_i$ and $l_i$ values that have minimized the cost function at i=m are then traced back to i=1, giving integer $a_i$ and $l_i$, for all samples of jth line. The process is performed for the next line j+1 until the displacement of the whole image is calculated. The 2D DP method gives integer axial and lateral displacement maps. In [40], we performed hierarchical search to obtain subsample axial displacement (the lateral displacement was not refined to subsample). DP is an efficient method for global optimization and has been used extensively in many applications in computer vision including solving for optimal deformable models [42]. In the next section, we propose an alternative method for calculating sub-sample axial displacement which is both faster and more robust than hierarchical DP.

B. 1D Analytic Minimization (AM)

Tissue deformations in ultrasound elastography are usually very small and therefore a subsample displacement estimation is required. We now develop a method that analytically minimizes a regularized cost function and gives the refined displacement field following the work presented in [16]. We first consider a specialization of (2) in which we only consider refining axial displacements to subsample level.

Having the integer displacements $a_i$ and $l_i$ from DP, it is desired to find $\Delta a_i$ values such that $a_i+\Delta a_i$ gives the value of the displacement at the sample i for i=1 ... m ($l_i$, $a_i$ and $\Delta a_i$ correspond to line j. Hereafter, wherever the displacements correspond to the jth line, j is omitted to prevent notation clutter). Such $\Delta a_i$ values will minimize the following regularized cost function:

$$C_j(\Delta a_i, \ldots, \Delta a_m) = \sum_{i=1}^{m} \{[I_1(i,j) - I_2(i+a_i+\Delta a_i, j+l_i)]^2 + \alpha_a(a_i+\Delta a_i - a_{i-1} - \Delta a_{i-1})^2 + \alpha_l(a_i+\Delta a_i - a_{i,j-1} - \Delta a_{i,j-1})^2]\} \quad (3)$$

where $\alpha_a>0$ and $\alpha_l>0$ are tunable axial and lateral regularization weights and subscript j−1 refers to the previous RF-line (adjacent RF-line in the lateral direction).

Substituting $I2(i+di+\Delta di)$ with its first-order Taylor expansion approximation around $d_i$, we have $$C_j(\Delta a_1, \ldots, \Delta a_m) = \sum_{i=1}^{m} \{[I_1(i,j) - I_2(i+a_i, j+l_i) - I'_2(i+a_i, j+l_i)\Delta a_i]^2 + \alpha_a(a_i+\Delta a_i - a_{i-1} - \Delta a_{i-1})^2 + \alpha_l(a_i+\Delta a_i - a_{i,j-1} - \Delta a_{i,j-1})^2]\} \quad (4)$$

where $I'_2$ is the derivative of the $I_2$ in the axial direction. The optimal $\Delta a_i$ values occur when the partial derivative of $C_j$ with respect to $\Delta a_i$ is zero. Setting $(\partial C_j)/(\partial \Delta a_i)=0$ for i=1 ... m we have $$(I'^2_2 + \alpha_a D + \alpha_l \hat{I})\Delta a_j = I'_2 e - (\alpha_a D + \alpha_l \hat{I})a_j + \alpha_l a_{j-1}, \quad (5)$$

$$D = \begin{bmatrix} 1 & -1 & 0 & 0 & \ldots & 0 \\ -1 & 2 & -1 & 0 & \ldots & 0 \\ 0 & -1 & 2 & -1 & \ldots & 0 \\ \vdots & & & & \ddots & \\ 0 & 0 & \ldots & 0 & -1 & 1 \end{bmatrix} \quad (6)$$

where $I'_2$=diag($I'_2(1+d_1, j+l_1) \ldots I'_2(m+dm, j+l_m)$), $\Delta a_j=[\Delta a_{1,j} \ldots \Delta a_{m,j}]^T$, $e=[e_1 \ldots e_m]^T$, $e_i=I_1(i,j)-I_2(i+d_i, j+l_i)$, $a_j=[a_{1,j} \ldots a_{m,j}]^T$, $\hat{I}$ is the identity matrix and $a_{j-1}$ is the total displacement of the previous line (i.e., when the displacement of the j−1th line was being calculated, $a_{j-1}$ was updated with $a_{j-1}+\Delta a_{j-1}$). $I'_2$, D and $\hat{I}$ are matrices of size m×m and $\Delta a$, e and a are vectors of size m.

Comparing 1D AM [as formulated in (5)] and 2D DP, they both optimize the same cost function. Therefore, they give the same displacement fields (up to the refinement level of the DP). In the next two subsections, we will further improve 1D AM.

1) Biasing the Regularization: The regularization term $\alpha_a(a_i+\Delta a_i - a_{i-1} - \Delta a_{i-1})^2$ penalizes the difference between $a_i+\Delta a_i$ and $a_{i-1}+\Delta a_{i-1}$, and therefore can result in underestimation of the displacement field. Such underestimation can be prevented by biasing the regularization by $\epsilon$ to $\alpha_a(a_i+\Delta a_i - a_{i-1} - \Delta a_{i-1} - \epsilon)^2$, where $\epsilon=(a_m-a_i)/(m-1)$ is the average displacement difference (i.e., average strain) between samples i and i−1. An accurate enough estimate of $d_m - d_1$ is known from the previous line. With the bias term, the right-hand side of (5) becomes $I'_2e - (\alpha_a D + \alpha_l \hat{I})a_j + \alpha_l(a_{j-1}+\Delta a_{j-1})+b$ where the bias term is $b=(\alpha_a[-\epsilon 0 \ldots 0\epsilon]^T$ (only the first and the last terms are nonzero) and all other terms are as before. In the other words, except for the first and the last equations in this system, all other m−2 equations are same as (5).

Equation (5) can be solved for $\Delta a_j$ in 4 m operations since the coefficient matrix $I'^2_2 + \alpha_a + \alpha_l \hat{I}$ is tridiagonal. Utilizing its symmetry, the number of operations can be reduced to 2 m. The number of operations required for solving a system with a full coefficient matrix is more than $m^3/3$, significantly more than 2 m.

2) Making Elastography Resistant to Outliers: Even with pure axial compression, some regions of the image may move out of the imaging plane and decrease the decorrelation. In such parts the weight of the data term in the cost function should be reduced. The data from these parts can be regarded as outliers and therefore a robust estimation technique can limit their effect. Before deriving a robust estimator for 66 d, we rewrite (4) as $$C(\Delta d) = \sum_{i=1}^{m} \rho(r_i) + R(\Delta d) \quad (7)$$

where $r_i=I_1(i)-I_2(i+d_i)-I'_2(i+d_i)\Delta d_i$ is the residual, $\rho(r_i)=r_i^2$ and R is the regularization term. The M-estimate of $\Delta d$ is $\Delta d=\arg\min_{\Delta d}\{\Sigma_{i=1}^{m}\rho(r_i)+R(\Delta d)\}$ where $\rho(r_i)$ is a robust loss function [43]. The minimization is solved by setting $\partial C/\partial \Delta d_i=0$ $$\rho'(r_i)\frac{\partial r}{\partial \Delta d_i} + \frac{\partial R(\Delta d)}{\partial \Delta di} = 0. \quad (8)$$

A common next step [44] is to introduce a weight function w, where $w(r_i).r_i=\rho'(r_i)$. This leads to a process known as "iteratively reweighted least squares" (IRLS) [45], which alternates steps of calculating weights $w(r_i)$ for $r_i=1 \ldots m$ using the current estimate of $\Delta d$ and solving (8) to estimate a new $\Delta d$ with the weights fixed. Among many proposed shapes for $w(\bullet)$, we compared the performance of Huber [44], [43]

$$w(r_i) = \begin{cases} 1 & |r_i| < T \\ \dfrac{T}{|r_i|} & |r_i| > T \end{cases} \quad (9)$$

and Cauchy [45]

$$w(r_i) = \frac{1}{1+(r_i/T)^2} \quad (10)$$

functions and discovered that the more strict Cauchy function (which decreases with inverse of the square of the residual) is more suitable in our application. To better discriminate outliers, we calculate the residuals r, at linear interpolation of the integer sample displacements provided by DP. With the addition of the weight function, (8) becomes $$(wI'^2_2 + \alpha_a D + \alpha_l \hat{I})\Delta a_j = wI'_2 e - (\alpha_a D + \alpha_l \hat{I})a_j + \alpha_l a_{j-1} + b \quad (11)$$

where $w=\text{diag}(w(r_1) \ldots w(r_m))$. This equation will converge to a unique local minimum after few iterations [45]. The convergence speed however depends on the choice of T, which in this work is defined manually. Since the Taylor approximation gives a local quadratic approximation of the original non-quadratic cost function, the effect of higher orders terms increase if $\Delta a_j$ is large. Assuming that DP gives the correct displacements, $\|\Delta a_j\|_\infty \leq \epsilon$ where $\|\cdot\|_\infty$ is the infinity norm and $\epsilon \leq 0.5$. In practice, however, $\epsilon \ll 0.5$ because the linear interpolation of the DP displacements (which is very close to the correct displacement) is used to calculate the residuals $r_i$. Therefore, a small value can be assigned to T in 1D AM provided that DP results are trusted.

The coefficient matrix $Q = w I'_2{}^2 + \alpha_a D + \alpha_l \hat{I}$ in (11) is the Hessian of the cost function C whose minimum is sought. This matrix is strictly diagonally dominant (i.e., $|q_{ii}| > \Sigma_{j \neq i} |q_{ij}|$ for all i where $q_{ij}$ is the i, jth element of Q), symmetric and all diagonal entries are positive. Therefore, it is positive definite, which means that setting the gradient of C to zero results in the global minimum of C (not in a saddle point, a local maximum or a local minimum) All of the 1D AM results presented in this work are obtained with one iteration of the above equation.

1D AM takes the integer axial and lateral displacement fields from DP and gives refined axial displacement. It inherits the robustness of DP and adds more robustness when calculating the fine axial displacements via IRLS. However, there are redundant calculations in this method which are eliminated in 2D AM as described next.

C. 2D Analytic Minimization (AM)

In 2D AM, we modify (2) to calculate subsample axial and lateral displacement fields simultaneously. The outline of our proposed algorithm is as follows.

1) Calculate the integer axial and lateral displacements of one or more seed RF-lines (preferably in the middle of the image) using DP [(2)]. Calculate the linear interpolation of the integer displacements as an initial subsample estimate.
2) Calculate subsample axial and lateral displacements of the seed RF-line using 2D AM, as explained below. Add the subsample axial and lateral displacements to the initial estimate to get the displacement of the seed line.
3) Propagate the solution to the right and left of the seed RF-line using the 2D AM method, taking the displacement of the previous line as the initial displacement estimate.

Benefits of 2D AM are two-fold. First it computes subsample displacements in both axial and lateral directions. Lateral strain contains important information from tissue structure that is not available from axial strain [31], [46], [47]. Second, it is only required to calculate the displacement of a single line using DP (the seed), eliminating the need to have the integer displacement map for the entire image. This is significant as in the 1D AM method, the initial step to calculate the 2D integer displacements using DP takes about 10 times more than the 1D AM.

Assume that initial displacement estimates in the axial direction, $a_i$, and in the lateral direction, $l_i$, are known for all $i = 1 \ldots m$ samples of an RF-line. Note that $a_i$ and $l_i$ are not integer; for the seed line they are the linear interpolation of the integer DP displacements and for the rest of the lines are the displacement of the previous line. It is desired to find $\Delta a_i$ and $\Delta l_i$ values such that the duple $a_i + \Delta a_i$, $l_i + \Delta l_i$ gives the axial and lateral displacements at the sample i. Such $(\Delta d_i, \Delta a_i)$ values will minimize the following regularized cost function:

$$C_j(\Delta a_1, \ldots, \Delta a_m, \Delta l_1, \ldots, \Delta l_m) = \quad (12)$$

$$\sum_{i=1}^{m} \{[I_1(i,j) - I_2(i + a_i + \Delta a_i, j + l_i + \Delta l_i)]^2 +$$

$$\alpha(a_i + \Delta a_i - a_{i-1} - \Delta a_{i-1})^2 +$$

$$\beta_a(l_i + \Delta l_i - l_{i-1} - \Delta l_{i-1})^2 + \beta'_l(l_i + \Delta l_i - l_{i,j-1})^2\}$$

where $I(i, j)$ is the ith sample on the jth RF-line. Since we perform the calculations for one RF-line at a time, we dropped the index j to simplify the notations: $a_i$, $l_i$, $\Delta a_i$, and $\Delta l_i$ are $a_{i,j}$, $l_{i,j}$, $\Delta a_{i,j}$, and $\Delta l_{i,j}$. $\Delta l_{i,j-1}$ is the lateral displacement of the previous RF-line (note that $l_{i,j-1}$ is the total lateral displacement of the previous line, i.e., when the displacement of the j−1th line was being calculated, $l_{i,j-1}$ was updated with $l_{i,j-1} + \Delta l_{i,j-1}$). Since in the first iteration $a_i$ and $l_i$ (the initial displacement estimates) are in fact the displacements of the previous RF-line, for the first iteration we have $l_{i,j-1} = l_i$. This simplifies the last term in the right-hand side to $\beta'_l \Delta l_i^2$. The regularization terms are $\alpha$, $\beta_\alpha$ and $\beta'_l$: $\alpha$ determines how close the axial displacement of each sample should be to its neighbor on the top and $\beta_\alpha$ and $\beta'_l$ determine how close lateral displacement of each sample should be to its neighbors on the top and left (or right if propagating to the left). If the displacement of the previous line is not accurate, it will affect the displacement of the next line through the last term in the right-hand side of (12). Although its effect will decrease exponentially with j, it will propagate for few RF-lines. Therefore, we set $$\beta'_l = \frac{\beta_l}{1 + |r_{i,j-1}|} \quad (13)$$

to prevent such propagation where $r_{i,j-1}$ is the residual associated with the displacement of the ith sample of the previous line. A large residual indicates that the displacement is not accurate and therefore its influence on the next line should be small, which is realized via the small weight $\beta'_l$. This is, in principle, similar to guiding the displacement estimation based on a data quality indicator [48]. The effect of the tunable parameters $\alpha$, $\beta_\alpha$ and $\beta_1$ is studied in Section III. Writing the 2D Taylor expansion of the data term in (12) around $(i+a_i, j+l_i)$ $$I_2(i+a_i+\Delta a_i, j+l_i+\Delta l_i) \approx I_2(i+a_i, j+l_i) + \Delta a_i I'_{2,a} + \Delta l_i I'_{2,l} \quad (14)$$

where $I'_{2,a}$ and $I'_{2,l}$ are the derivatives of the $I_2$ at point $(i+a_i, j+l_i)$ in the axial and lateral directions respectively. Note that since the point $(i+a_i, j+l_i)$ is not on the grid ($a_i$ and $l_i$ are not integer), interpolation is required to calculate $I'_{2,a}$ and $I'_{2,l}$. We propose a method in Section II-C1 that eliminates the need for interpolation. The optimal $(\Delta a_i, \Delta l_i)$ values occur when the partial derivatives of $C_j$ with respect to both $\Delta a_i$ and $\Delta l_i$ are zero. Setting $(\partial C_j)/(\partial \Delta a_i) = 0$ and $(\partial C_j)/(\partial \Delta l_i) = 0$ for $i = 1 \ldots m$ and stacking the 2 m unknowns in $\Delta d = [\Delta a_1\ l_1\ \Delta a_2\ \Delta l_2 \ldots \Delta a_m\ \Delta l_m]^T$ and the 2 m initial estimates in $d = [a_1\ l_1\ a_2\ l_2 \ldots a_m\ l_m]^T$ we have $$(I'^2_2 + D_1 + D_2)\Delta d = I'_2 e - D_1 d, \quad (15)$$

$$D_1 = \begin{bmatrix} \alpha & 0 & -\alpha & 0 & 0 & 0 & \ldots & 0 \\ 0 & \beta_a & 0 & -\beta_a & 0 & 0 & \ldots & 0 \\ -\alpha & 0 & 2\alpha & 0 & -\alpha & 0 & \ldots & 0 \\ 0 & -\beta_a & 0 & 2\beta_a & 0 & -\beta_a & \ldots & 0 \\ 0 & 0 & -\alpha & 0 & 2\alpha & 0 & \ldots & 0 \\ \vdots & & & & & & \ddots & \\ 0 & 0 & 0 & \ldots & -\alpha & 0 & \alpha & 0 \\ 0 & 0 & 0 & \ldots & 0 & -\beta_a & 0 & \beta_a \end{bmatrix}$$

where $D_2 = \text{diag}(0, \beta'_l, 0, \beta'_l, \ldots 0, \beta'_l)$ is a diagonal matrix of size 2 m×2 m, $I'_2{}^2 = \text{diag}\, \mathfrak{I}'^2(1) \ldots \mathfrak{I}'^2(m)$ is a symmetric tridiagonal matrix of size 2 m×2 m with $$\mathfrak{I}'^2(i) = \begin{bmatrix} I'^2_{2,a} & I'_{2,a}I'_{2,l} \\ I'_{2,a}I'_{2,l} & I'^2_{2,l} \end{bmatrix} \quad (16)$$

blocks on its diagonal entries where $I'_{2,a}$ and $I'_{2,l}$ are the derivatives of the $I_2$ at point $(i+a_i j+l_i)$ in the axial and lateral directions $$I'_2 = \text{diag}(I'_{2,a}(1), I'_{2,l}(1), I'_{2,a}(2), I'_{2,l}(2) \ldots I'_{2,a}(m), I'_{2,l}(m)) \quad (17)$$

where $I'_{2,a}(i)$ and $I_{2,l}(i)'$ are calculated at point $(i+a_i, j+l_i)$, and $\mathbf{e} = [e_1 e_1 e_2 e_2 \ldots e_m]^T$, $e_i = I_1(i,j) - I_2(i+a_i, j+l_i)$.

We make four modifications to (15). First, we take into account the attenuation of the ultrasound signal with depth. As the signal gets weaker with depth, the first term in the right-hand side of (15) ($I'_2\mathbf{e}$) gets smaller. This results in increasing the share of the regularization term in the cost $C_j$ and therefore over-smoothing the bottom of the image. The attenuation of the ultrasound signal [49] reflected from the depth d is $\zeta(d) = e^{-2\log(10) a_t f_0 d/20}$ where $a_t$ is the frequency dependent attenuation coefficient of tissue and is equal to 0.63 dB/cm/MHz for fat [49], $f_0$ is the center frequency of the wave (in MHz) and d is in cm. Having the exponential attenuation equation, the attenuation level at sample i will be $$\zeta_i = x^{-i}, \, x = e^{\frac{1540 \times 10^2 a_t f_0 \log(10)}{20 f_s \times 10^6}}, \, i = 1 \ldots m \quad (18)$$

where $1540 \times 10^2$ is the speed of sound in tissue (in cm/sec) and $f_s$ is the sampling rate of the ultrasound system (in MHz). This is assuming that the TGC (time gain control) is turned off. Otherwise, the TGC values should be taken into account in this equation. Let the 2 m×2 m diagonal matrix Z be $Z = \text{diag}(\zeta_1, \zeta_1, \zeta_2, \zeta_2 \ldots \zeta_m, \zeta_m)$. To compensate for the attenuation, we multiply the $D_1$ and $D_2$ matrices in (15) by Z, and therefore reduce the regularization weight with depth. As we will show in Sections III and IV, the regularization weight can vary substantially with no performance degradation. Therefore approximate values of the speed of sound and attenuation coefficient will suffice. Second, we add a bias term in the regularization similar to the 1D case. Here we only bias the axial displacement since the difference between the lateral displacements of the points on a RF-line is very small, usually less than 4 RF-lines. Third, we exploit the fact that, because the tissue is in contact with the ultrasound probe, the axial displacement of the top of the image is zero relative to the probe (the lateral displacement of the top of the image is not zero as tissue might slip under the probe). Therefore, we enforce the axial displacement of the first sample to be zero by changing the first row of $D_1$, $I'_2{}^2$, and $I'_2$. Fourth, we make the displacement estimation robust via IRLS using the Cauchy function (10). Similar to 1D AM, T is selected manually. For the first (seed) RF-line, a small value can be selected for T if DP results are trusted. For the next lines, the value of $\Delta d$ determines the accuracy of the Taylor expansion 14: for a small $\Delta d$, the residuals of the inliers are small and therefore a small T can be chosen, while for a large $\Delta d$ the inliers might give large residuals and therefore a large value for T is required. Since the tissue motion is mostly continuous, $\Delta d$ mostly depends on the lateral sampling of the image (i.e., the number of A-line per cm). Therefore if many A-lines are given per cm of the image width, a small value of T will give the optimum results. Since the amplitude of signal is decreasing due to attenuation, we decrease the IRLS parameter T with depth by multiplying it with $\zeta_i$ at each sample i. With these modifications, (15) becomes $$WI'_2{}^2 + ZD_1 + ZD_2)\Delta d = WI'_2 \mathbf{e} - ZD_1 d + s \quad (19)$$

where $W = \text{diag}(0, w(r_1), w(r_2), w(r_2) \ldots w(r_m), w(r_m))$ (i.e., $W_{2i,2i} = W_{2i-1,2i-1} = w(r_i)$ for $i = 1 \ldots m$ except for $W_{1,1} = 0$ which guarantees the displacement of the first sample to be zero) is the weight function determined by the residuals $r_i = I_1(i,j) - [I_2(i+d_i, j+a_i) + \Delta d_i I'_{2,z} + \Delta a_i I'_{2,x}]$, w is as before (10), the bias term s is a vector of length 2 m whose all elements are zero except the 2 m−1th element: $s_{2m-1} = \alpha\epsilon$, and $\epsilon = (d_m - d_1)/(m-1)$ is as before. Similar to (11), the coefficient matrix $Q = WI'_2{}^2 + ZD_1 + ZD_2$ is strictly diagonally dominant, symmetric and all the diagonal entries are positive. Therefore $Q$ is positive definite which means that solving (19) results in the global minimum of the cost function C. The updated displacement field (axial and lateral) will be $d + \Delta d$.

Equation (19) can be solved for $\Delta d$ in 9 m operations since the coefficient matrix $WI'_2{}^2 + ZD_1 + ZD_2$ is pentadiagonal and symmetric. This number is again significantly less than $((2m)^3/(3)$, the number of operations required to solve a full system.

Figure 2B:
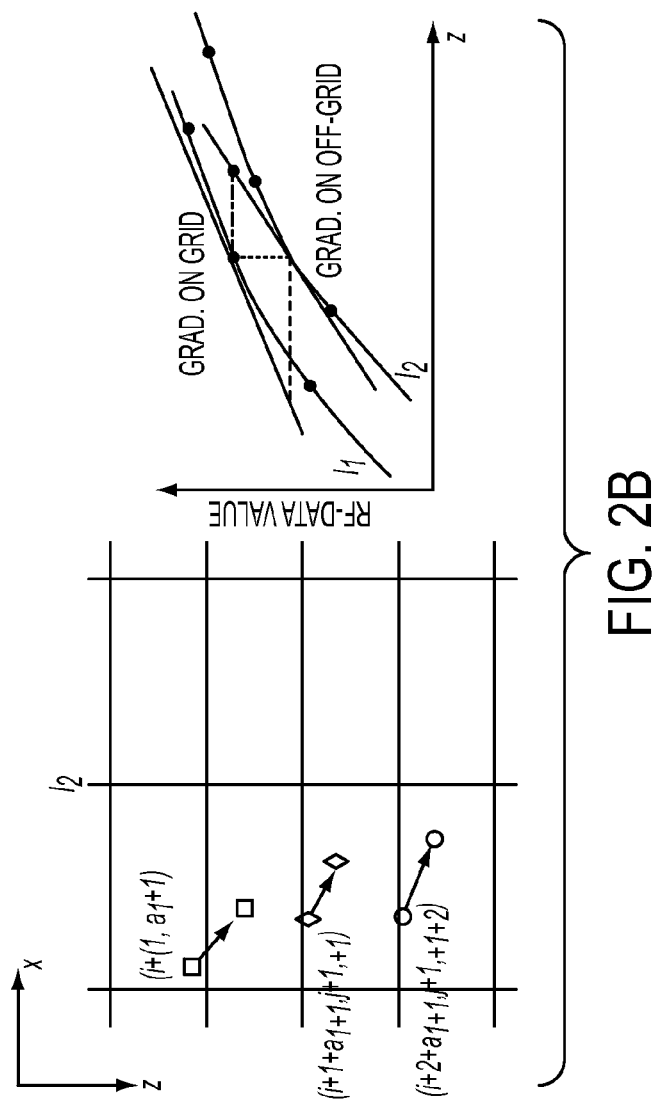
FIGS. 2A and 2B are schematic illustrations to explain some concepts of methods of processing ultrasound data and ultrasound systems according to an embodiment of the current invention.
Figure 2A:
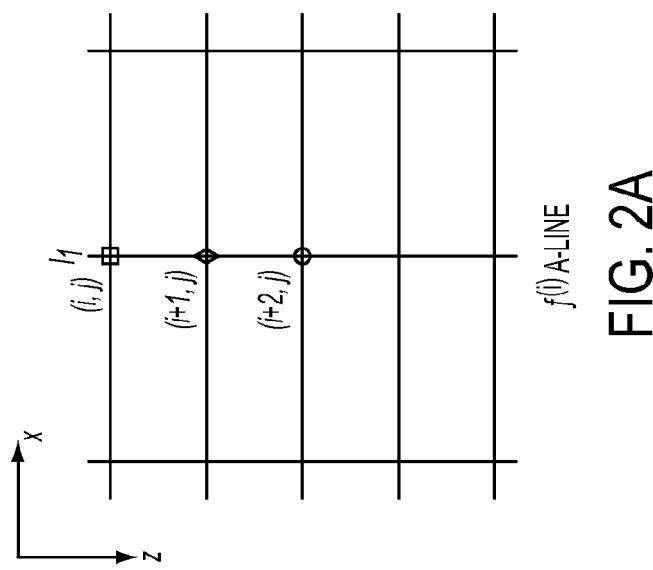

1) Inverse Gradient Estimation: With the subsample initial displacement field, the Taylor expansion should be written around off-grid points, which requires calculation of image gradient at these points [matrices $I'_2{}^2$ and $I'_2$ in (19)]. In FIG. 2(A), this is equivalent to calculating gradient of $I_2$ on the off-grid marks. There are two disadvantages associated with this: 1) it requires interpolation of the gradients, and 2) the image gradient should be recalculated after each iteration. As proposed by [44], [50], image gradient can be instead calculated at on-grid locations on image 1 in the following way.

Consider two problems: 1) to find the matches for grid points on I1 having the initial off-grid estimates on $I_2$, and 2) to find the matches for the off-grid points on $I_2$ having the initial grid estimates on $I_1$. For both problems, $I_2$ values must be interpolated on the off-grid values. However, the second problem does not require interpolation of the image gradient since the Taylor expansion is written around grid points of $I_1$ [FIG. 2(B)]. It is shown in [51] that the two techniques converge to the same results. Therefore, on one hand inverse gradient calculation is both faster and easier to implement, and on the other hand it causes no performance degradation. Exploiting this, (19) becomes $$(WI'_1{}^2 + ZD_1 + ZD_2)\Delta d = WI'_1 \mathbf{e} - ZD_1 d + s \quad (20)$$

where $I'_1{}^2$ and $I'_1$ are now calculated on the grid points of image 1.

All the 2D AM results presented in this work are obtained using (20). For the seed line where the initial estimate might be inaccurate, this equation is iterated multiple times (about 10 times). For all other lines, this equation is iterated only once.

D. Strain Estimation Using Kalman Filter

Strain estimation requires spatial derivation of the displacement field. Since differentiation amplifies the signal noise, least squares regression techniques are commonly used to obtain the strain field. Adjacent RF-lines are usually processed independently in strain calculation. However, the strain value of each pixel is not independent from the strain value of its neighboring pixels. The only exception is the boundary of two tissue types with different mechanical properties where the strain field is discontinuous. We use the prior of piecewise strain continuity via a Kalman filter to improve the quality of strain estimation. Although locations with strain discontinuity are limited, we will develop a technique to take such discontinuities into account.

We first calculate the strain using least squares regression. Each RF-line is first differentiated independently: for each sample i, a line is fitted to the displacement estimates in a window of length 2 k+1 around i, i.e., to the samples i−k to i+k. The slope of the line, $z_{i,j}$, is calculated as the strain measurement at i. The center of the window is then moved to i+1 and the strain value $z_{i+1,j}$ is calculated. We reuse overlapping terms in calculation of $z_{i,j}$ and $z_{i+1,j}$, and therefore the running time is independent of the window length 2 k+1. Having $z_{i,j}$ for i=1 . . . m, and j=1 . . . n, we propose the following algorithm based on Kalman filter to take into account the prior of strain continuity.

zi, j are the noisy measurements of the underlying strain field $\epsilon_{i,j}$. Since the zi, j values are calculated using axial windows, we apply the Kalman filter in the lateral direction. Let $r_j$ be the Gaussian process noise and $s_j$ be the Gaussian measurement noise to be removed. We have [52], [41]

$$\epsilon_{i,j} = \epsilon_{i,j-1} + r_{i,j} \tag{21}$$

$$z_{i,j} = \epsilon_{i,j} + s_{i,j}. \tag{22}$$

Let $\hat{\epsilon}^-_{i,j}$ (note the super minus) be our a priori strain estimate from the process prior to step j [i.e., from the (21)] and $\hat{\epsilon}_{i,j}$ be our a posteriori strain estimate at step j given measurement $z_j$. Let also the variances of $\hat{\epsilon}^-_{i,j}$ and $\hat{\epsilon}_{i,j}$ be respectively $p^-$ and p. The time update (i.e., prior estimation) equations will be [41]

$$\hat{\epsilon}^-_{i,j} = \hat{\epsilon}_{i,j-1} \tag{23}$$

$$p^-_{i,j} = p_{i,j-1} + \sigma_r^2 \tag{24}$$

where $\sigma_r^2$ is the variance of the process noise r. $p_{i,j-1}$ is initialized to zero for the first sample j=1. The measurement update equations will be [41]

$$\hat{\epsilon}_{i,j} = \hat{\epsilon}^-_{i,j} + \frac{p^-_{i,j}}{p^-_{i,j} + \sigma_s^2}(z_{i,j} - \hat{\epsilon}^-_{i,j}) \tag{25}$$

$$p_{i,j} = \left(1 - \frac{p^-_{i,j}}{p^-_{i,j} + \sigma_s^2}\right) p^-_{i,j} \tag{26}$$

where $\sigma_s^2$ is the variance of the measurement noise s. Note that since both the state $\epsilon_{i,j}$ and measurement $z_{i,j}$ are scalars, all the update equations only require scalar operations. We estimate $\sigma_r^2$ and $\sigma_s^2$ as following. Let the mean (calculated using a Gaussian kernel of standard deviation of $\sigma_G$=0.6 sample) of the strain values in 3×3 blocks around samples (i, j−1) and (i, j) be $\mu_{j-1}$ and $\mu_j$, respectively. Then $\sigma_r^2$ is [52]

$$\sigma_r^2 = (\mu_{j-1} - \mu_j)^2. \tag{27}$$

This is a reasonable estimate of $\sigma_r^2$ as it tries to capture the difference between pixel values at adjacent RF-lines. If the difference between the mean strain values is high, less weight is given to the a priori estimate. This space-variant estimation of the model noise provides a better match to local variations in the underlying tissue leading to a greater noise reduction. $\sigma_s^2$ is the variance of $z_{i,j}$ measurements in the entire image and is constant throughout the image.

The strain estimation algorithm can be summarized as following.

1) Perform least squares regression in the axial direction for each RF-line. Generate a (noisy) strain image Z whose pixel i,j is $z_{i,j}$. This step ensures continuity in the axial direction.
2) Apply the Kalman filter to the noisy strain image Z in the lateral direction. Generate a (denoised) strain image whose pixel i, j is $\hat{\epsilon}_{i,j}$. This step ensures continuity in the lateral direction.

Both steps are applied once and are not iterated. We show in the experimental results how the Kalman filter removes the noise from the strain image with minimal blurring, owing to the model noise update (27).

III. Simulation Results

Field II [53] and ABAQUS (Providence, R.I.) software are used for ultrasound simulation and for finite element simulation. Many scatterers are distributed in a volume and an ultrasound image is created by convolving all scatterers with the point spread function of the ultrasound and adding the results using superposition. The phantom is then meshed and compressed using finite element simulation, giving the 3D displacement of each node of the mesh. The displacement of each scatterer is then calculated by interpolating the displacement of its neighboring nodes. Scatterers are then moved accordingly and the second ultrasound image is generated. The displacement and strain fields are then calculated using the AM methods and are compared with the ground truth. The unitless metric signal-to-noise ratio (SNR) and contrast to noise ratio (CNR) are also calculated to assess the performance of the AM method according to $$CNR = \frac{c}{N} = \sqrt{\frac{2(\bar{s}_b - \bar{s}_t)^2}{\sigma_b^2 + \sigma_t^2}}, \quad SNR = \frac{\bar{s}}{\sigma} \tag{28}$$

where $\bar{s}_t$ and $\bar{s}_b$ are the spatial strain average of the target and background, $\sigma_t^2$ and $\sigma_b^2$ are the spatial strain variance of the target and background, and $\bar{s}$ and $\sigma$ are the spatial average and variance of a window in the strain image, respectively.

The parameters of the ultrasound probe are set to mimic commercial probes. The probe frequency is 7.27 MHz, the sampling rate is 40 MHz and the fractional bandwidth is 60%. A Hanning window is used for apodization, the single transmit focus is at 22.5 mm, equi-distance receive foci are from 5 to 45 mm at each 5 mm, the transmit is sequential, and the number of active elements is 64.

Two simulated phantoms are generated. The first phantom is 50×10×55 mm and the second one is 36×10×25 mm Respectively 5×10⁵ and 1.4×10⁵ scatterers with Gaussian scattering strengths [54] are uniformly distributed in the first and second phantom, ensuring more than 10 scatterers [55] exist in a resolution cell.

Figure 7A:
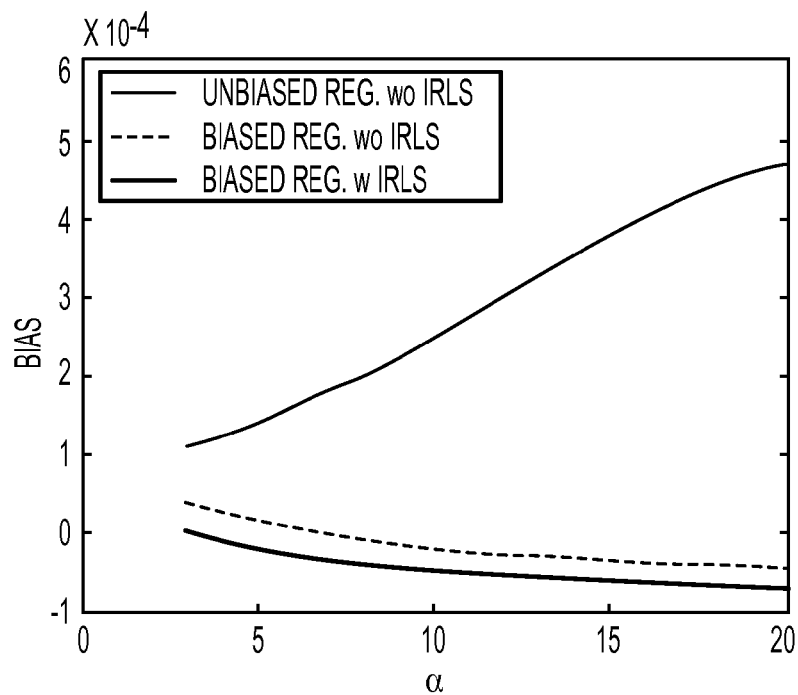
FIGS. 7A and 7B show Bias and Variance of the lateral strain as a function of the axial regularization weight $\alpha$. The ground truth axial and lateral strain fields are respectively uniform 2% and $2\nu$% fields ($\nu=0.49$ is the Poisson's ratio). The solid blue curve corresponds to unbiased regularization and the dashed and solid black curves correspond to the biased regularization. IRLS is not used in the solid blue and dashed black curves. (7A) Bias. (7B) Variance.

The mechanical properties of both phantoms, required for finite element simulation, is assumed to be isotropic and homogeneous. The first phantom is uniform while the second phantom contains a circular hole filled with blood that can move out-of-plane, simulating a blood vessel in tissue [FIG. 7(A)]. The scatterers are distributed in the vessel, also with the same intensity and distribution as the surrounding material. A uniform compression in the z direction is applied and the 3D displacement field of phantoms is calculated using ABAQUS. The Poisson's ratio is set to $\nu$=0.49 in both phantoms to mimic real tissue [56], [57] which causes the phantoms to deform in x and y directions as a result of the compression in the z direction.

Figure 3A:
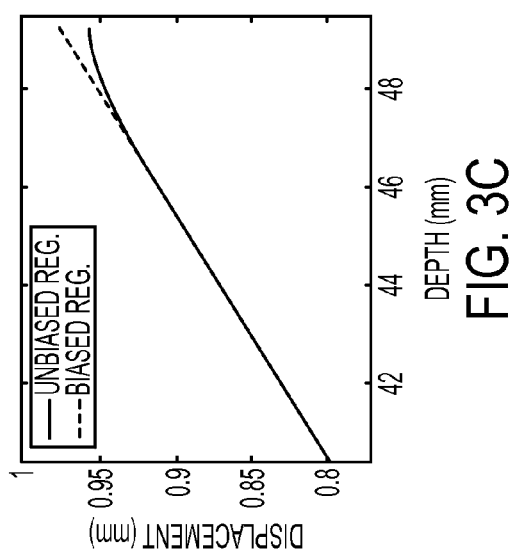
FIGS. 3A-3F show axial strain estimation in the first simulated phantom. (3A) The SNR values corresponding to the unbiased regularization calculated in the entire image. (3B) Schematic plot showing the underestimation of the displacement (Data+reg. curve) with unbiased regularization (refer to the text). (3C), (3D). The calculated displacements at the bottom of a RF-line at 2% strain and 6% strain levels respectively with biased and unbiased regularization terms. The ground truth matches the displacement given by the biased regularization almost perfectly, and therefore is not shown (3C) and (3D) not to block the biased regularization results. The length of the RF-line is 2560 (49.3 mm). (3E) The SNR values corresponding to the unbiased regularization calculated by omitting the bottom 300 samples of the image. 3F The SNR values corresponding to the biased regularization calculated in the entire image. Note that the scale of the SNR in graph 3A is much smaller than that of graphs (3E) and (3F). (3A) Unbiased reg. Entire image. (3B) Schematic displacements. (3C) Calculated displacements at 2% strain. (3D) Calculated displacements at 6% strain. (3E) Unbiased reg. Top of the image. (3F) Biased reg. Entire image.
Figure 3B:
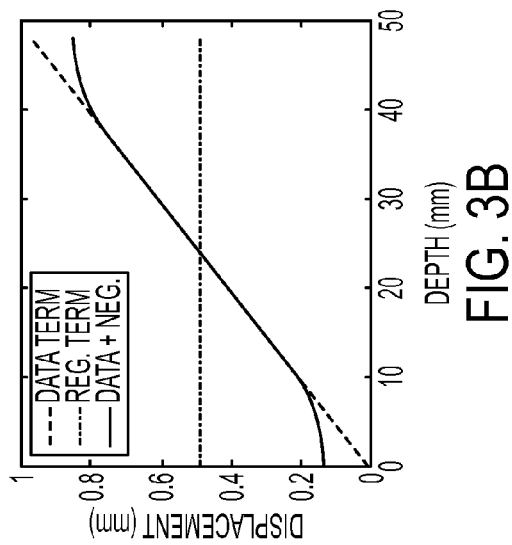
Figure 3C:
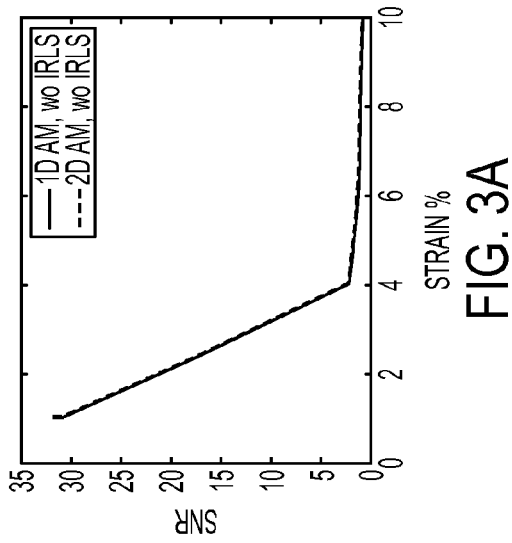
Figure 3D:
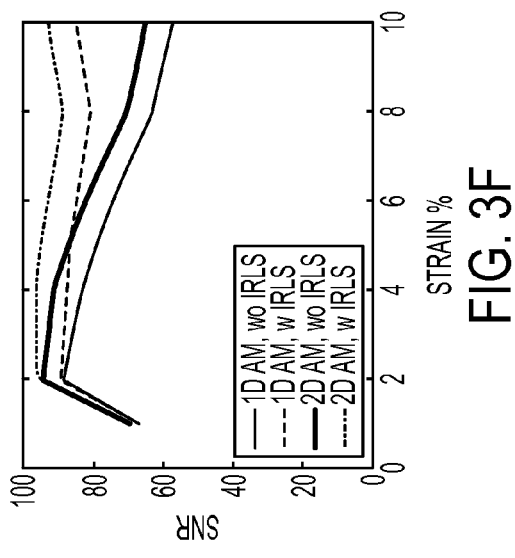
Figure 3E:
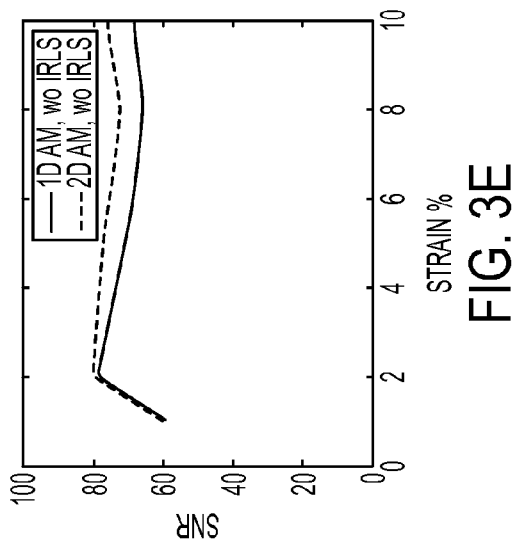
Figure 3F:
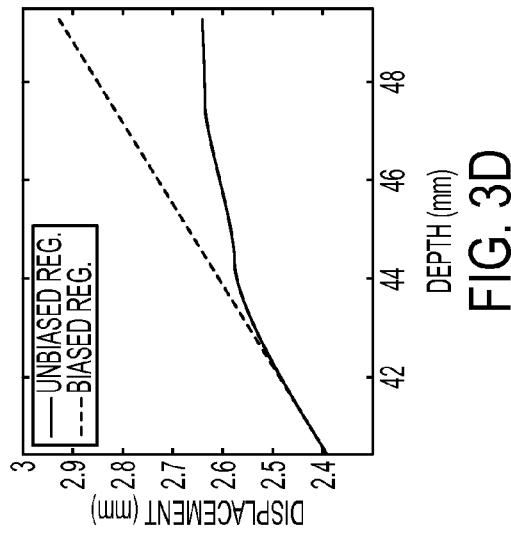

The first phantom undergoes compressions in the z direction to achieve strain levels of 1%-10%. FIG. 3 shows the SNR of the axial strain of the 1D AM and 2D AM methods [the window for SNR calculation covers the entire strain image in FIGS. 3A and (3F)]. The sharp drop of the SNR with strain in graph (3A) is mainly due to the strain underestimation in the bottom part of the image. It can be explained as following. The unbiased regularization term tries to force constant displacement [dashed-dotted red line in (3B)]. Assuming an ideal noiseless case where the data term gives a smooth ramp displacement [dashed black line in (3B)], minimizing the cost function (which is the summation of the data and the regularization terms) will underestimate the displacement at the two ends [solid blue line in (3B)]. This underestimation decays exponentially moving towards the center of the image. This artifact is shown in the simulation experiment at 2% and 6% strain levels in FIGS. 3C and (3D). Since we exploit the fact that the axial displacement of the first sample is zero (Section II-C), the underestimation does not happen in the top of the image. Biasing the regularization prevents this artifact, as is shown in FIGS. 3C and 3D. The AM method with or without the bias term gives the same result away from the bottom of the image: part (3E) shows that if we ignore 300 (5.8 mm) samples at the bottom of the image, the SNR will not drop sharply unlike in FIG. 3A. FIG. 3F shows the SNR of the AM methods with biased regularization calculated in the entire image. The SNR at 1% strain in parts FIGS. 3E and 3F is the same. At higher strain levels, the strain underestimation propagates more into the middle of the image, and therefore the SNR decreases at higher strain levels in graph (3E). FIG. 3E shows 2D AM gives slightly better axial strain compared to 1D AM. IRLS slightly increases the SNR. However, we will see in the simulation results of the second phantom that in the presence of outliers significant improvement in SNR and CNR is achieved using IRLS.

Figure 4:
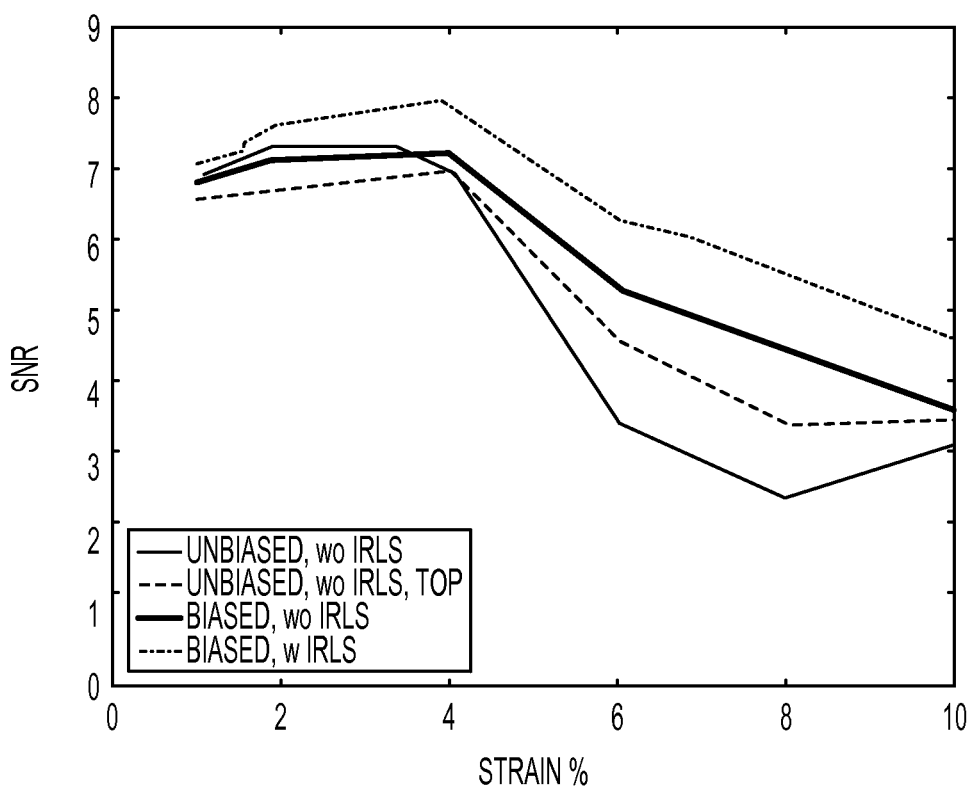
FIG. 4 shows lateral strain estimation using the 2D AM method in the first simulated phantom.

The SNR of the lateral strain field is much lower than that of the axial strain field (FIG. 4). Unbiased regularization gives the lowest SNR, mainly due to artifacts in the bottom of the image. Similar to the axial strain, the SNR improves as 300 samples from the bottom of image are omitted from the SNR calculation (results not shown).

Figure 5A:
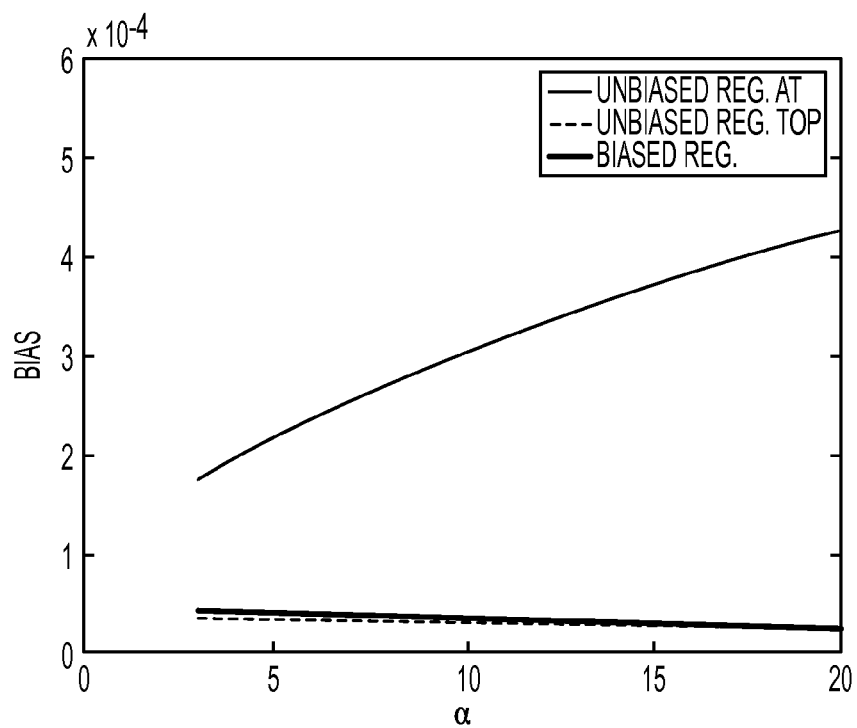
FIGS. 5A and 5B show Bias and Variance of the axial strain as a function of the axial regularization weight $\alpha$. The ground truth axial and lateral strain fields are respectively uniform 2% and $\nu$% fields ($\nu=0.49$ is the Poisson's ratio). The solid blue and dashed black curves both correspond to unbiased regularization and the solid black curve corresponds to the biased regularization. In the solid blue and solid black curves, the entire image is included in the calculation of the bias and noise. In the dashed black curve the bottom part of the strain field which suffers from high bias [FIG. 3B] is excluded from the calculation of the bias and noise. 1D AM and 2D AM have very similar bias and variance. The curves with and without IRLS are also very close. Therefore each curve corresponds to 1D AM or 2D AM with or without IRLS. (3A) Bias. (3B) Variance.
Figure 5B:
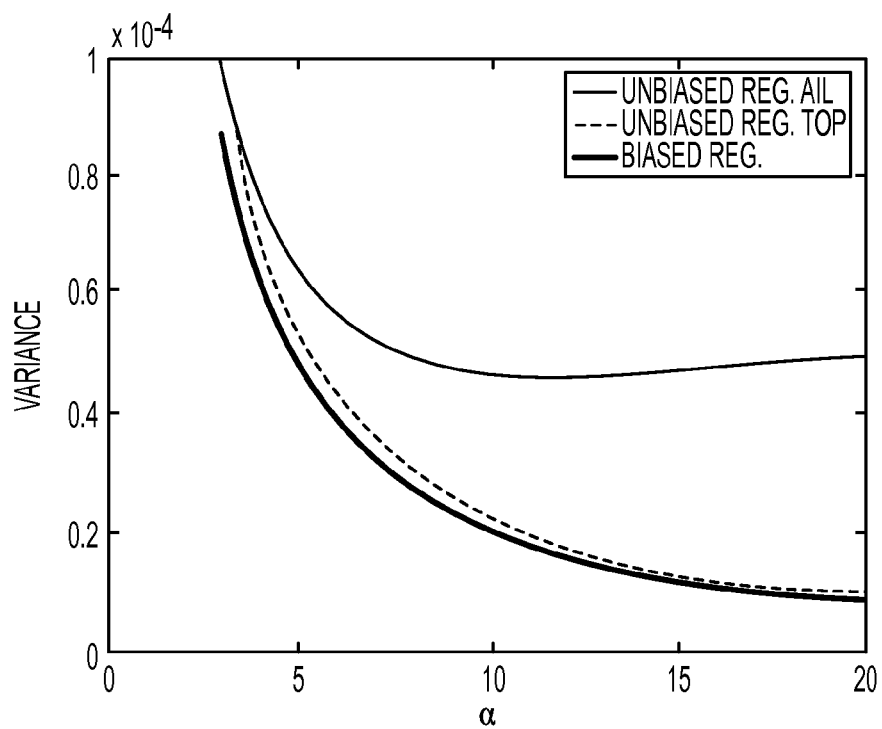
Figure 6A:
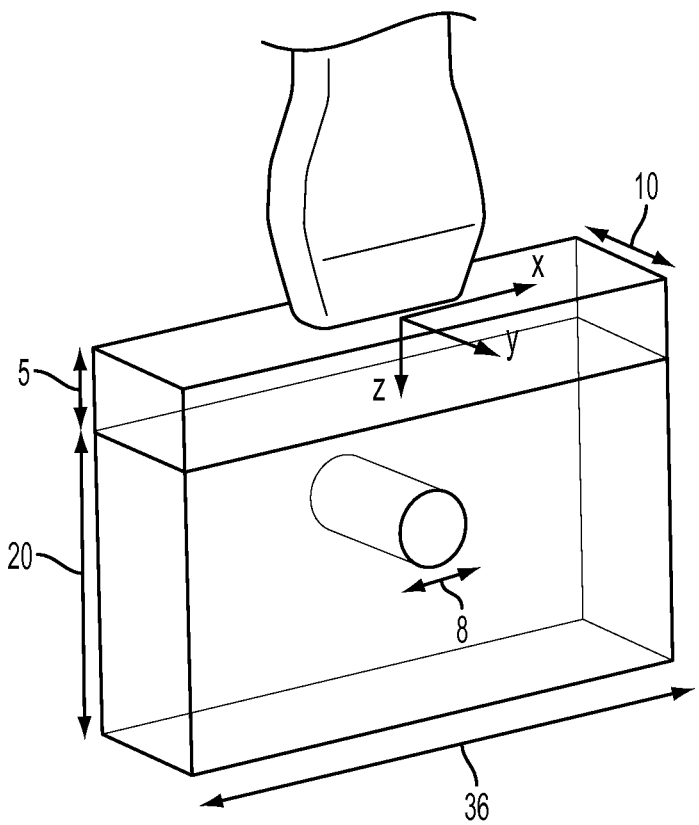
FIG. 6A-6D: Measurements in (6A) are in mm. In (6B), a scatterer is shown in the bottom left part as a red dot. Its displacement is calculated by interpolating the displacements of its three neighboring nodes on the mesh. The target (circular) and background (rectangular) windows for CNR calculation of (6D) are shown in (6C). (6A) Simulation phantom. (6B) Finite element mesh. (6C) Finite element strain. (6D) CNR.
Figure 6B:
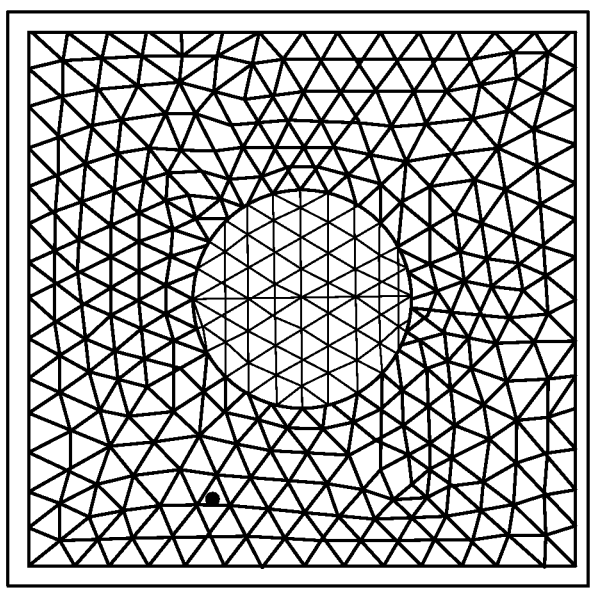
Figure 6C:
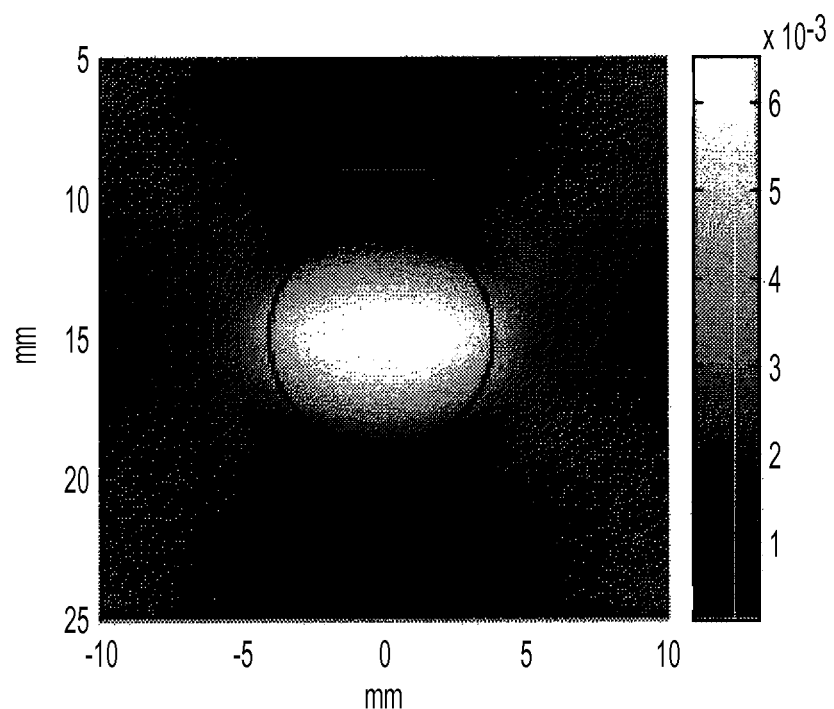
Figure 6D:
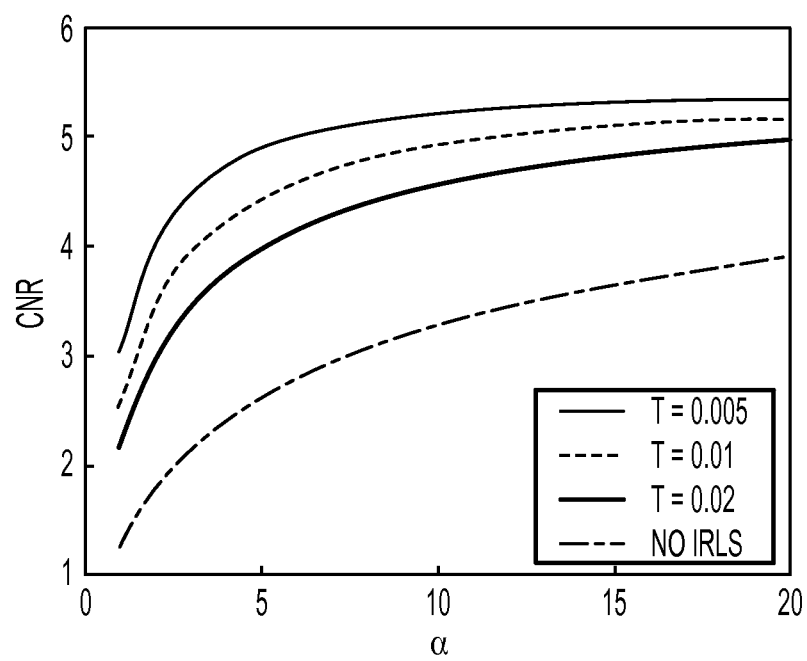

The effect of the regularization weights on bias and variance of the axial strain image at 2% ground truth axial strain is shown in FIG. 5. The blue curves show the bias and variance of the entire strain image obtained with unbiased regularization. It shows the tradeoff between the bias and variance: increasing the regularization weight increases the bias and decreases the variance. The variance starts to increase at $\alpha \approx 12$ which is caused by the underestimation of the strain at the bottom of the image [the artifact in FIG. 3(c)]. If we exclude the bottom 300 samples of the strain image from the bias and variance calculation (the black dashed curve), we see a consistent drop of variance as $\alpha$ is increased. The black curves show the bias and variance of the entire strain image obtained with biased regularization. Biasing the regularization causes the bias to decrease as the regularization weight $\alpha$ is increased which is a nonstandard behavior. It can be explained by the simple ground truth strain field which is uniform, exactly what the regularization term is trying to achieve. Even in the unbiased case, only the bias of the bottom part of the strain field increases as $\alpha$ is increased (i.e., in the bias plot, the blue curve increases while the black dashed curve decreases). Therefore, one cannot conclude from this experiment that higher $\alpha$ is beneficial to both bias and variance. To prove this, we designed a simulation study where the underlying axial strain field continuously varied with depth and the lateral and out-of-plane strains were zero (such strain field is not physically realizable). We observed that the absolute value of the bias monotonically increases with $\alpha$ with both unbiased and biased regularizations. To save space, we do not present the full results here. Similar curves for the lateral strain field is shown in FIG. 6.

Figure 7B:
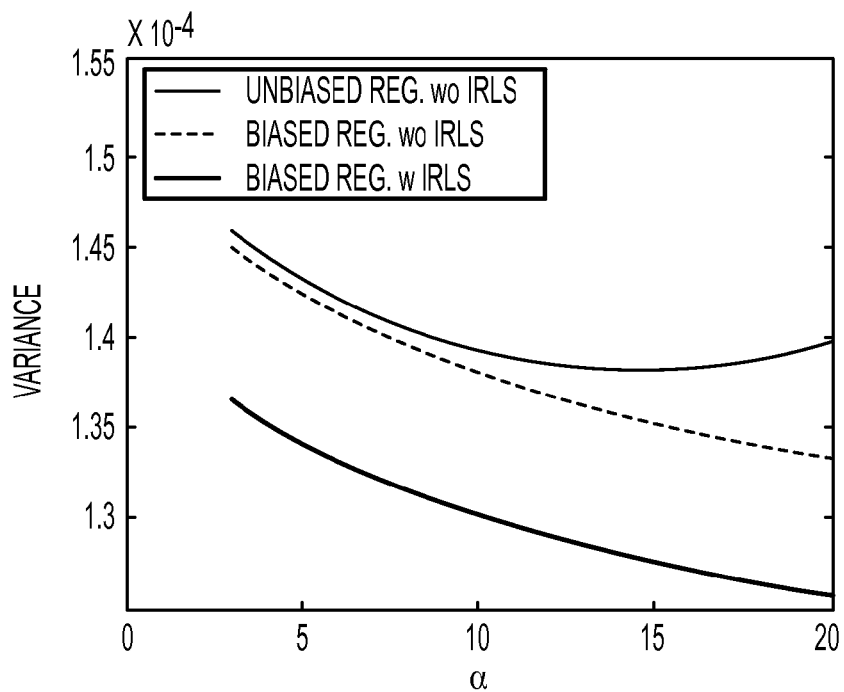

The second simulation experiment is designed to show the effect of smoothness weight and IRLS threshold CNR when the correlation is lower in parts of the image due to fluid motion. The phantom contains a vein oriented perpendicular to the image plane (FIG. 7). The background window for CNR calculation is located close to the target window to show how fast the strain is allowed to vary, a property related to the spatial resolution. The maximum CNR with IRLS is 5.3 generated at T=0.005 and $\alpha_a$=38, and without IRLS is 4.8 at $\alpha_a$=338. Such high $\alpha_a$ value makes the share of the data term in the cost function very small and causes over-smoothing.

A. Displacement Simulation

Figure 8A:
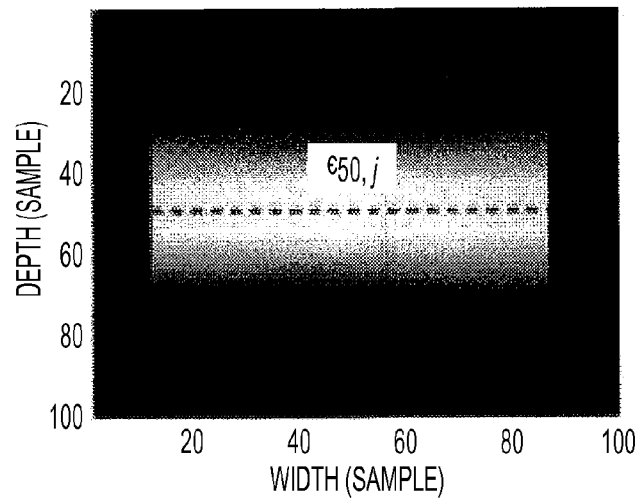
FIGS. 8(a)-8(e): (a) shows the strain field calculated using least squares regression of the uncontaminated displacement field. (b) depicts the strain field calculated using least squares regression of the contaminated displacement field. (c) shows the strain field calculated from the noisy measurements of (b) using the proposed Kalman filter (KF in (b) and (c) refers to Kalman filter). The pixels of images in (a) to (c) are respectively the ground truth (unavailable) strain values $\epsilon_{i,j}$, the noisy measurements $z_{i,j}$, and posterior strain values $\hat{e}_{i,j}$. The brightness scale in (a)-(c) is the same. (d), (e) are the strain estimation at the horizontal line shown in (a)-(c). (d) is magnified in (e) around the step. The Kalman filter removes the noise while keeping the image sharp, due to the variable model noise of (27). (a) Ground truth strain. (b) Strain without KF. (c) Strain with KF. (d) Strain estimate. (e) Strain estimates.
Figure 8B:
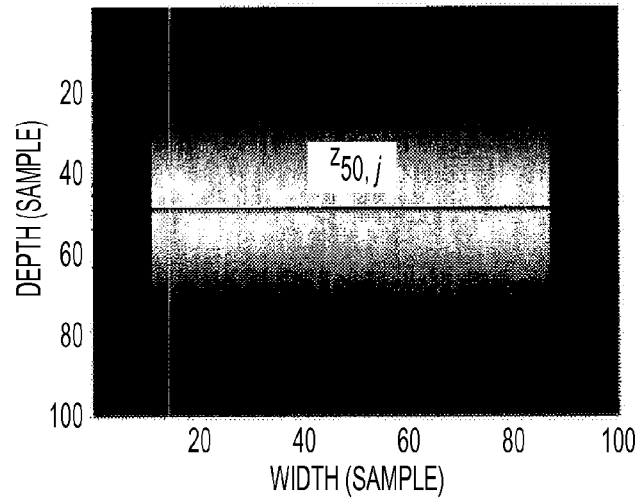
Figure 8C:
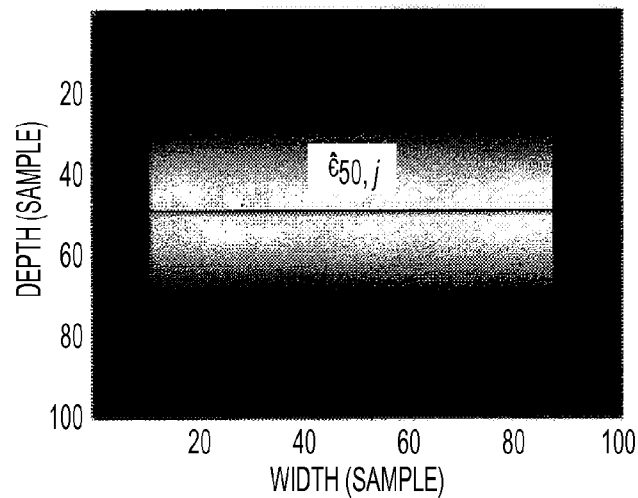
Figure 8D:
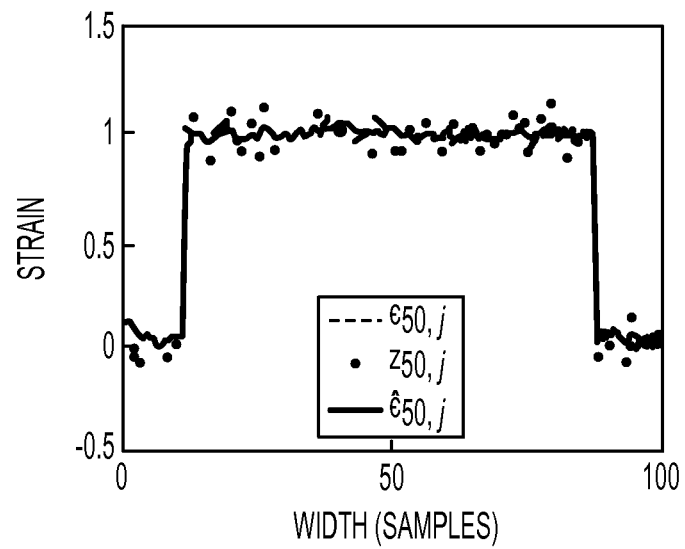
Figure 8E:
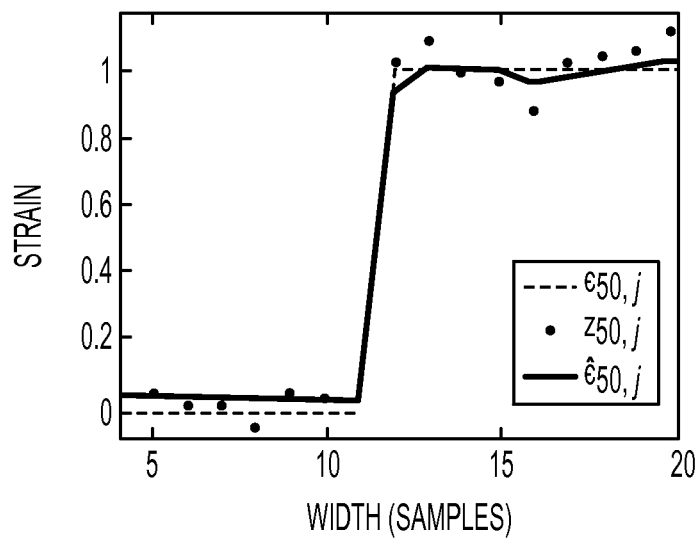

To study the performance of the Kalman filter, we simulate a displacement field of size 100×100 samples whose strain image (calculated using least squares regression) is as shown in FIG. 8A. One hundred samples in the axial direction corresponds to approximately 1.9 mm (assuming 40 MHz sampling rate), and 100 samples in the lateral direction corresponds to 10-25 mm depending on the probe. To be consistent with the notations of Section II-D, let $\epsilon_{i,j}$ denote the strain values of the uncontaminated image in (8A). We then contaminate the displacement field with a Gaussian noise with standard deviation of 1.5 samples, and perform least squares regression to calculate the noisy estimates $z_{i,j}$ [FIG. 8B]. We then apply the Kalman filter as described in Section II-D to the noisy estimates $z_{i,j}$ in the lateral direction (i.e., row-by-row). The posterior estimates of the strain values, $\hat{\epsilon}_{i,j}$ are shown in (FIG. 8C). The strain values of the shown line in FIGS. 8A-8C (at i=50 samples) is shown in FIG. 8D and 8E [The plot in (8D) around the step in magnified in (8E)]. The Kalman filter formulation is eliminating the noise without over-smoothing the strain image. This is due to the model variance update (27). We note that although displacement is generally continuous in tissue, its spatial derivation (strain) is not: at the boundary of two tissues with different elasticity moduli, strain field is discontinuous.

IV. Experimental Results

For experimental evaluation, RF data is acquired from an Antares Siemens system (Issaquah, Wash.) at the center frequency of 6.67 MHz with a VF10-5 linear array at a sampling rate of 40 MHz. Only the 2D AM method is used in the experimental results. Phantom results and patient trials are presented in this section. The tunable parameters of the 2D AM algorithm are set to $\alpha$=5, $\beta_a$=10, $\beta_l$=0.005 and T=0.2 [(12) and (20)], and the tunable parameters of the DP (run for the seed RF-line in the 2D AM algorithm) are $\alpha_a$=$a_l$=0.15 (1) in all the phantom results (except if specified otherwise). In the patient results, all the parameters are the same except for $\beta_a$ which is increased to $\beta_a$=20 because the data is noisier. The strain images in all the patient trials are obtained using the least squares regression and Kalman filtering as described in Section II-D.

A. Phantom Results

1) Effect of Regularization on Residuals: The cost function of the AM method (7) is composed of residuals (i.e., the data term) and the regularization terms. The AM method minimizes this summation. Therefore the AM method will not necessarily minimize the residuals. We now show that the data term alone is nonconvex and has many local minima. Adding the regularization term will eliminate many of the local minima and makes optimization of the data term easier. This is in addition to the effect of regularization that makes the displacement field smooth, a generally desired attribute.

Figure 9D:
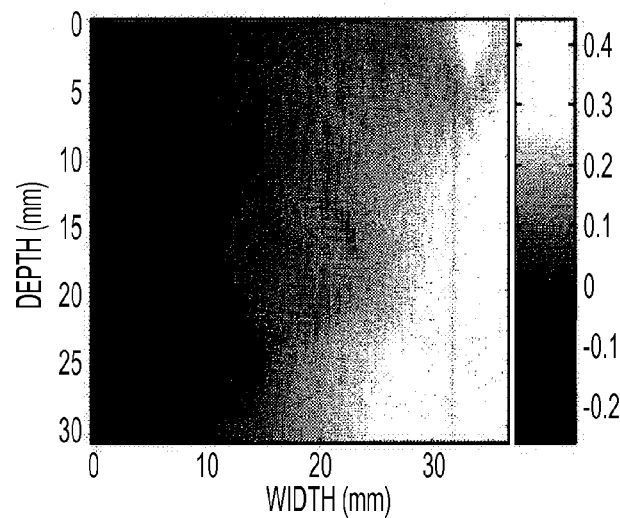

The effect of regularization on the residuals is studied using experimental data. An elastography phantom (CIRS elastography phantom, Norfolk, Va.) is compressed 0.2 in axially using a linear stage, resulting in an average strain of 6%. Two RF frames are acquired corresponding to before and after the compression. The Young's elasticity modulus of the background and the lesion under compression are respectively 33 kPa and 56 kPa. The displacement map is calculated using the 2D AM method and the residuals corresponding to the displacement map are obtained. FIGS. 9A-9C show the axial and lateral strains at such a high strain rate (minimum of 2% and maximum of 11%). The mean and median of the residuals $p(r_i)$ in the entire image is shown in FIG. 9D. One could expect the graph to monotonically increase as the regularization weight $\alpha$ increases, since the difference between the objective function C and the residuals $\Sigma_{i=1}^{m} p(r_i)$ is increased as $\alpha$ is increased. However, the residual values are very high at very low $\alpha$. Therefore, numerical minimization of $\Sigma_{i=1}^{m} p(r_i) + R(\Delta d)$ gives a smaller value for $\Sigma_{i=1}^{m} p(r_i)$ compared to trying to directly minimize $\Sigma_{i=1}^{m} p(r_i)$. This indicates that the nonregularized cost function is not quasi-convex and is very hard to minimize.

2) Resolution of the Strain Images Generated With AM: The effect of the regularization on spatial resolution is evaluated experimentally using the experimental setup of the previous experiment. The compression is set to 0.1 in in this experiment. FIG. 10A shows the strain image obtained by compression the lesion with the Young's modulus of 56 kPa. Spatial resolution is evaluated using modulation transfer function (MTF), an established method for estimating the spatial resolution of medical imaging systems that was relatively recently extended to elastography [58]. The spatial resolution of the reconstructed images is determined with a three-step approach [59], [60]. First, the edge spread function is computed by averaging the pixel values across the background-inclusion interface [the line in FIG. 10A]. Second, the line spread function (LSF) is computed by differentiating the edge spread function. Third, the MTF is determined by computing the Fourier transform of the LSF and normalizing the resulting function to zero spatial frequency $$MTF(k) = \frac{\Xi(k)}{\Xi(0)}. \tag{29}$$

FIG. 10C shows the MTF for five different normalization coefficients respectively. Strain results are obtained with a regression window of length 2 k+1=65 [Section II-D]. Increasing the regularization weight is adversely affecting spatial resolution. Spatial resolution is defined as the spatial frequency when the value of MTF is 0.1. At $\alpha=1$, $\alpha=2$ and $\alpha=4$ this value is respectively 2 cycles/mm, 1 cycles/mm, and 0.5 cycles/mm. In addition to $\alpha$, this value also depends on the length of the regression window 2 k +1.

3) Image Quality Versus Axial and Lateral Sampling Rates of the RF-Data: Sampling rate of the RF-data usually ranges from 20 to 50 MHz depending on the hardware of the device. The number of the A-lines provided in an image also varies significantly. In addition, bandwidth limitations of the data transfer can impose limits on the size of the image for real-time operations. In this study, we downsample the RF-data by a factor of 2-4 in the axial direction and by a factor of 2-8 in the lateral direction. FIGS. 11A-11G show axial and lateral displacement and strain images of the CIRS elastography phantom undergoing maximum axial strain of 5%. Axial sampling rate can be reduced by a factor of 2 without significant impact on the strain image quality [part (h)]. Downsampling the images in the lateral direction by a factor of 4 results the CNR of the axial and lateral strain images to drop respectively 12% (from 16.3 to 14.3) and 56% (from 2.55 to 1.13) as shown in (i). While the axial strain is robust to the number of A-line in the image even at a high strain level of 5%, the lateral strain is sensitive to it (i). Similar study with lower axial strain levels shows that as the axial strain decreases, higher downsampling rates in both axial and lateral directions are possible without a large impact on the results.

Figure 9E:
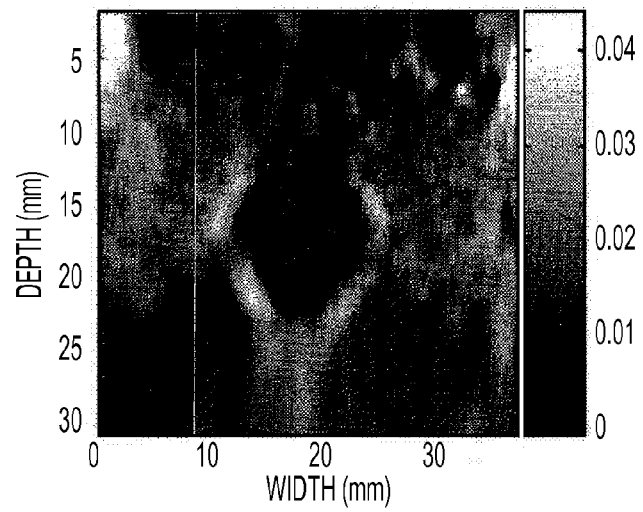
Figure 9F:
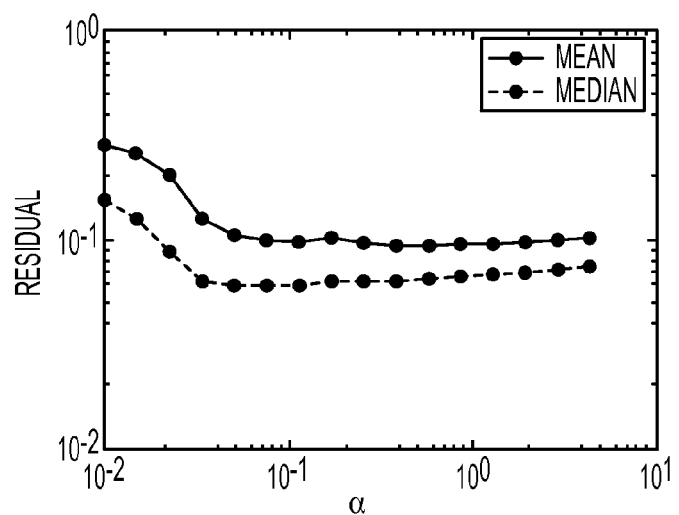
Figure 11G:
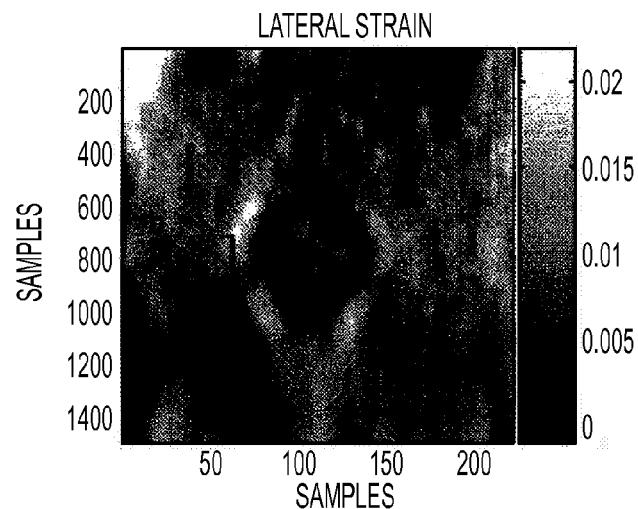
Figure 11H:
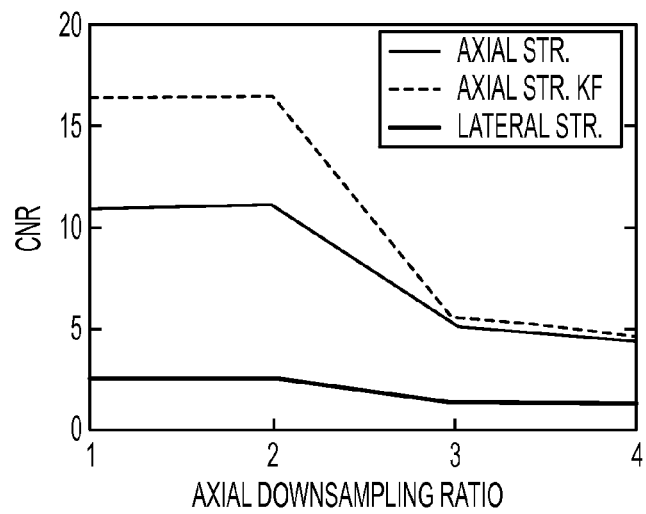
Figure 11I:
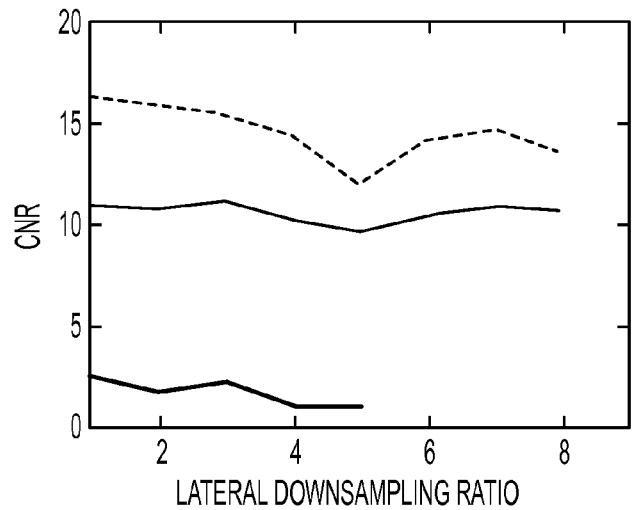
Figures 12A, 12B, 12C:
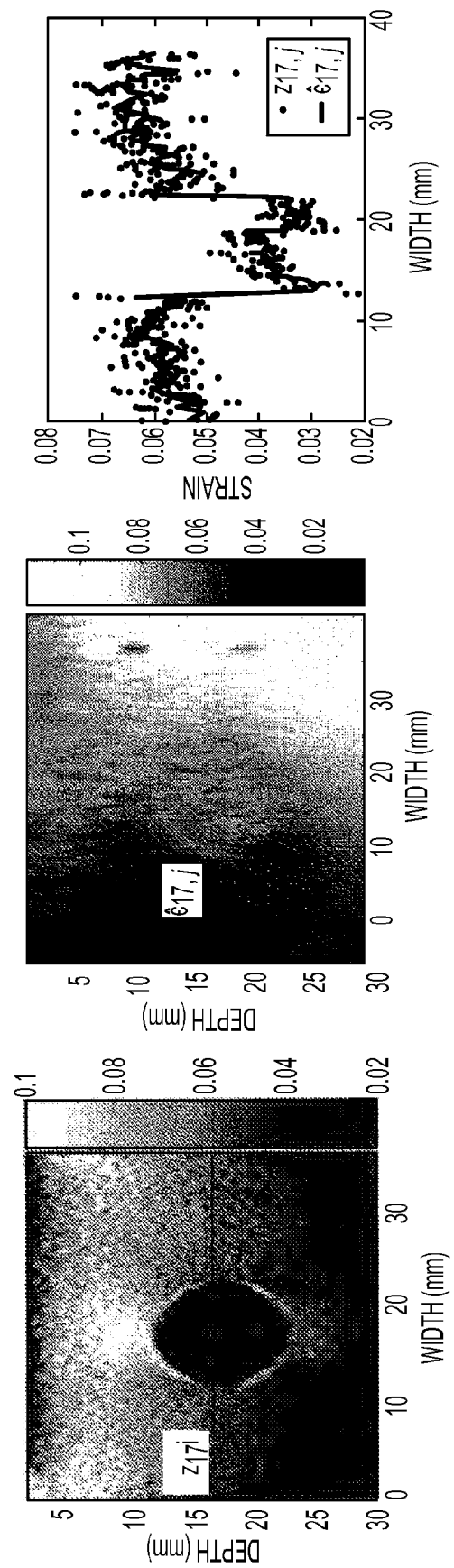
FIG. 12A-12C: Shows the axial strain field calculated by least squares regression of the noisy displacement field. (12B) depicts the strain field calculated from the noisy measurements of (12A) using the proposed Kalman filter (KF in (12A) and (12B) refers to Kalman filter). The pixels of images in (12A) and (12B) are respectively the least squares measurements $z_{i,j}$, and posterior strain values $\hat{e}_{i,j}$. (12C) shows the strain estimation at the 17 mm deep horizontal line shown in (12A) to (12B). The Kalman filter removes the noise while keeping the image sharp, due to the variable model noise of (27). (12A) Strain without KF. (12B) Strain with KF. (12C) Strain plots.
Figure 13A:
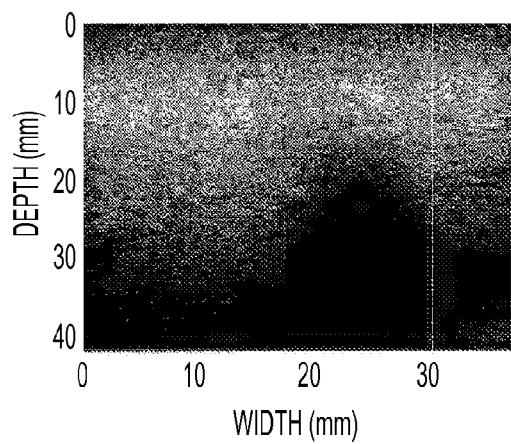
FIGS. 13(a)-13(l) show in vivo images of the thermal lesion produced by RF ablation therapy of liver cancer. All images acquired after ablation. First, second, and third rows correspond to the first, second and third patients respectively. The thermal lesion shows in (b), (f) and (j) as dark, surrounded by normal tissue in white. The lateral displacement images are shown in number of samples (they do not immediately carry anatomical information). In (b), (d), (f), (h), (j), and (l) the delineated thermal lesions is shown. The nonunity aspect ratio in the axes of the B-mode and strain images should be considered when comparing them to the CT scans. (a) B-mode patient 1. (b) Axial strain. (c) Lateral displacement. (d) CT patient 1. (e) B-mode patient 2. (f) Axial strain. (g) Lateral displacement. (h) CT patient 2. (i) B-mode patient 3. (j) Axial strain. (k) Lateral displacement. (l) CT patient 3.
Figure 13B:
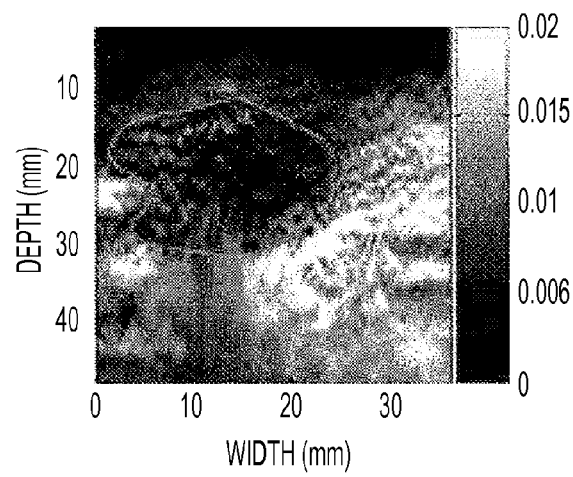
Figure 13C:
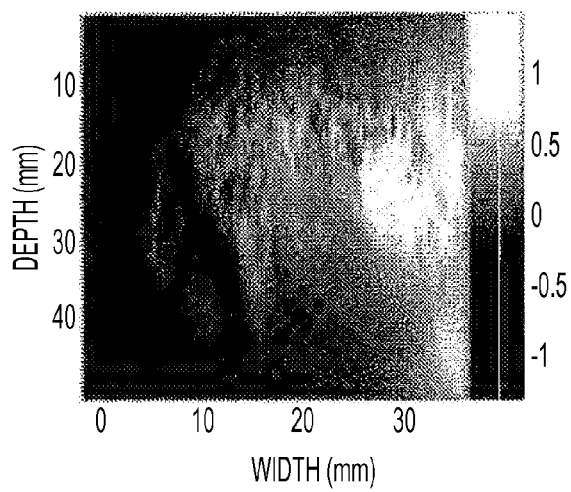
Figure 13D:
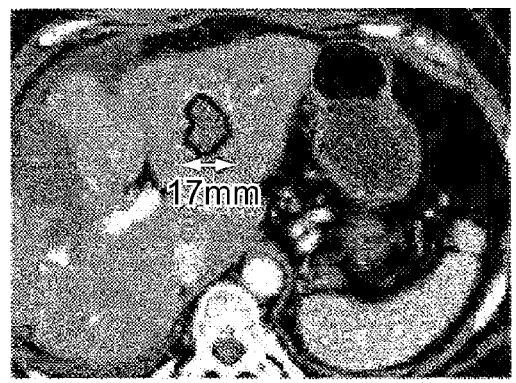
Figure 13E:
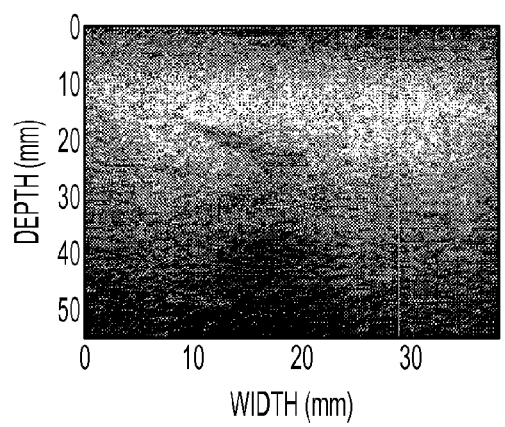
Figure 13F:
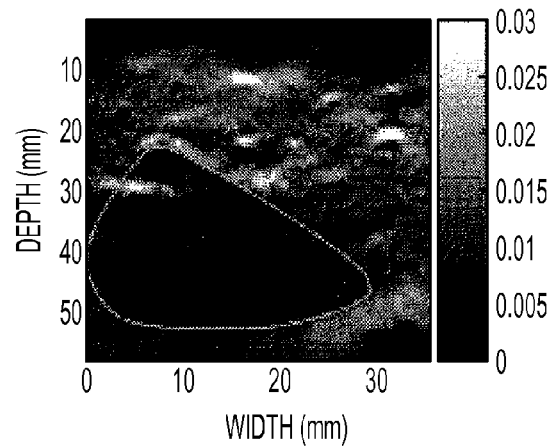
Figure 13G:
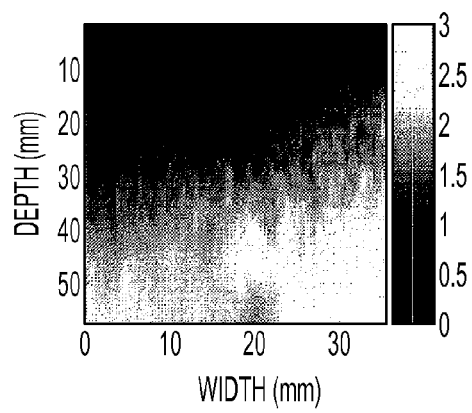
Figure 13H:
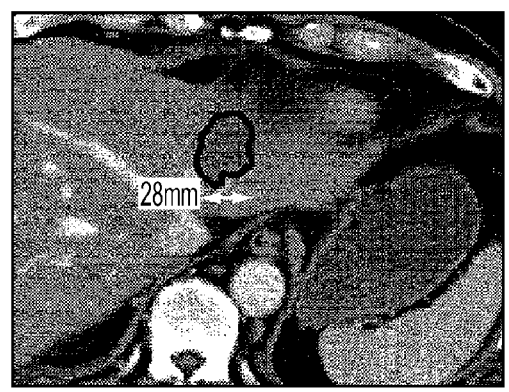
Figure 13I:
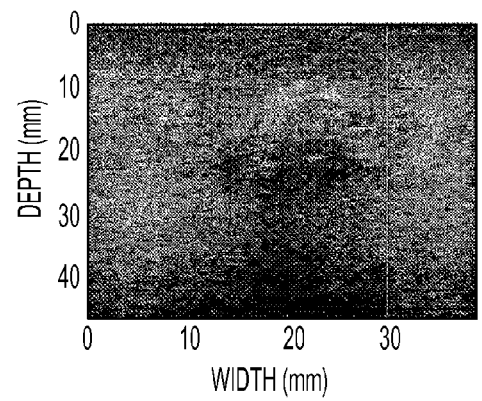
Figure 13J:
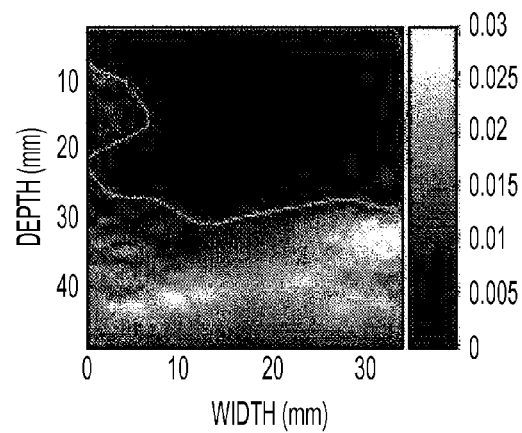
Figure 13K:
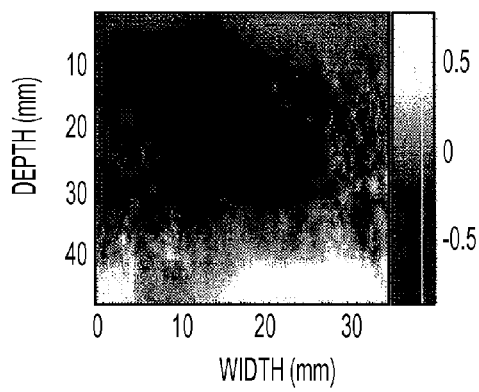
Figure 13L:
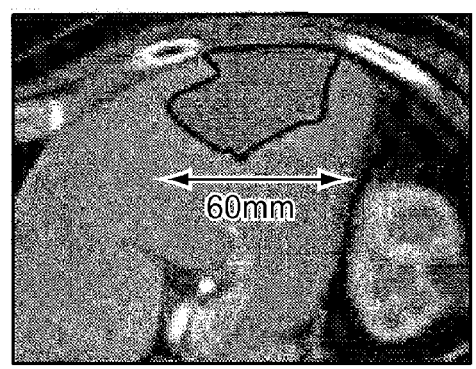

4) Kalman Filter: The performance of the Kalman filter is studied using the RF-data used in FIG. 9. The linear least squares differentiation technique is applied to the axial displacement field calculated with 2D AM, resulting in $z_{i,j}$ [FIG. 12A]. The Kalman filter is then applied to $z_{i,j}$ measurements of (12A), giving the posterior $\hat{\epsilon}_{i,j}$ measurements of (b). Comparing the strain values at a horizontal line of FIGS. 12A and 12B, the noisy $z_{i,j}$ measurements are smoothed in the lateral direction using the proposed Kalman filter, with minimal blurring of the edge.

B. Clinical Study

Seven patients undergoing open surgical radiofrequency (RF) thermal ablation for primary or secondary liver cancer were enrolled between Feb. 6, 2008 and Jul. 28, 2009. All patients enrolled in the study had unresectable disease and were candidates for RF ablation following review at our institutional multidisciplinary conference. Patients with cirrhosis or suboptimal tumor location were excluded from the study. All patients provided informed consent as part of the protocol, which was approved by the institutional review board. RF ablation was administered using the RITA Model 1500 XRF generator (Rita Medical Systems, Fremont, Calif.). Strain images are generated offline. Some preliminary results are published in [15].

We show the results from only four patients due to space limitations. FIG. 13 shows the B-mode scan, the strain images and CT scans performed after RF ablation. Tissue is simply compressed freehand at a frequency of approximately 1 compression per 2 s with the ultrasound probe without any attachment. The shadow in FIG. 13A at 20 mm depth is produced by the thermal lesion. Note that it is not possible to ascertain the size and position of the thermal lesions from B-mode images. In addition, the thermal lesion has different appearances in the three B-scans. However, the thermal lesions show very well as hard lesions in the strain images. After gross correlation of the post ablation CT scan and the thermal lesion in the strain images, the size of the lesion seems to correspond well. However, a more rigorous validation of the size and shape of the ablated lesion in the elastography image is underway using nonrigid registration of CT and ultrasound images. To the best of our knowledge, this is also the first demonstration of the success of elastography in imaging the thermal lesion in an in vivo human experiment.

Figure 14A:
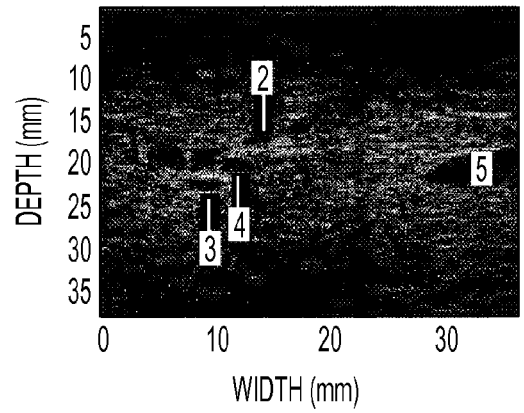
FIGS. 14A-14G show in vivo images of the fourth patient before RF ablation. In (14A), the left anterior branch of portal vein is marked as 1 and 2 and has low pressure and therefore compresses easily. Arteries (marked as 3 and 4) and the middle hepatic vein (marked as 5) however pulsate with the heart beat and may have low or high pressure. (14B) and (14C) both show the axial strain from the same location before ablation. They are calculated at two different phases of the heart beat. The cancer tumor is discernible in (14B) and (14C) (regardless of the systolic or diastolic blood pressure), and its boundary is shown. 1 and 2 [as marked in (14A)] correspond to the high strain area in both (14B) and (14C). Since 3,4, and 5 [as marked in (14A)] pulsate, they may look hard [as in (14B)] or soft [as in (14C)]. (14D) shows the lateral displacement. The tumors is not visible in this image. (14E) shows the motion of the probe and the variation in the diameter of the arteries due to the heart beat (refer to the text). (14F) is the arterial phase and (14G) is the venous phase contrast CT images. The numbers 1-5 mark the same anatomy as (14A) B-mode pre-ablation. (14B) Axial strain pre-ablation. (14C) Axial strain pre-ablation. (14D) Lateral displacement pre-ablation. (14E). (14F) CT pre-ablation. (14G) CT pre-ablation.
Figure 14B:
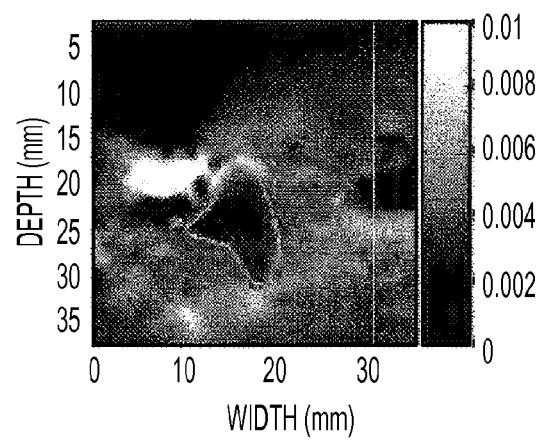
Figure 14C:
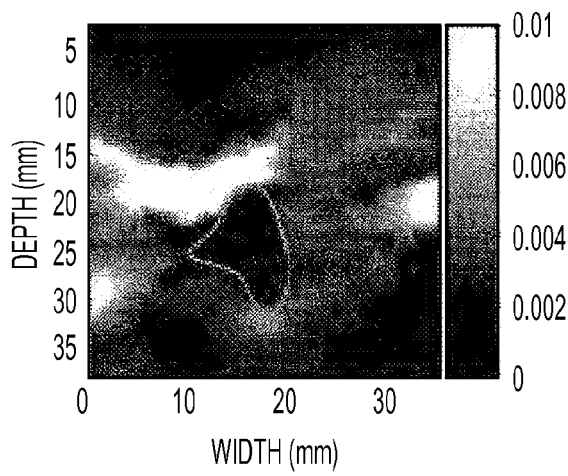
Figure 14D:
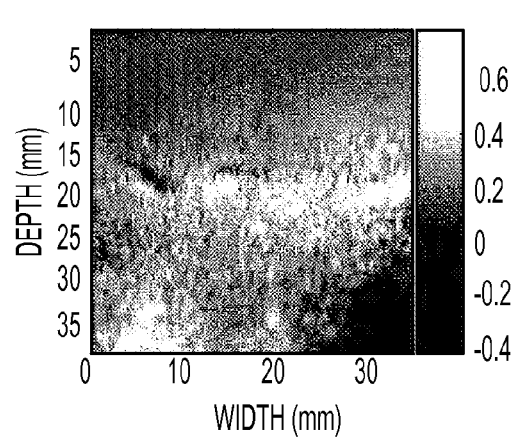
Figure 14E:
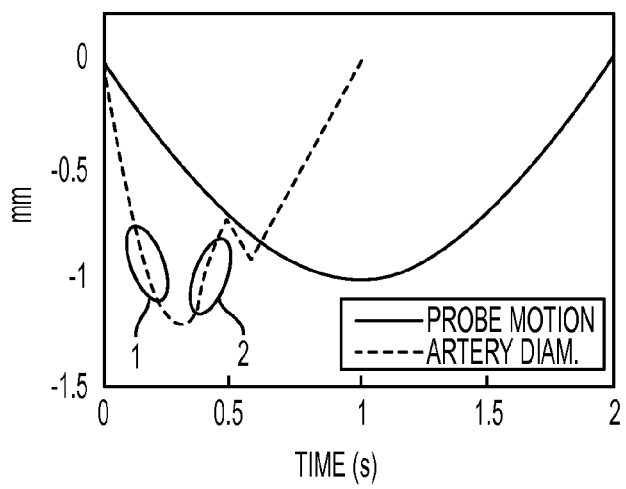
Figure 14F:
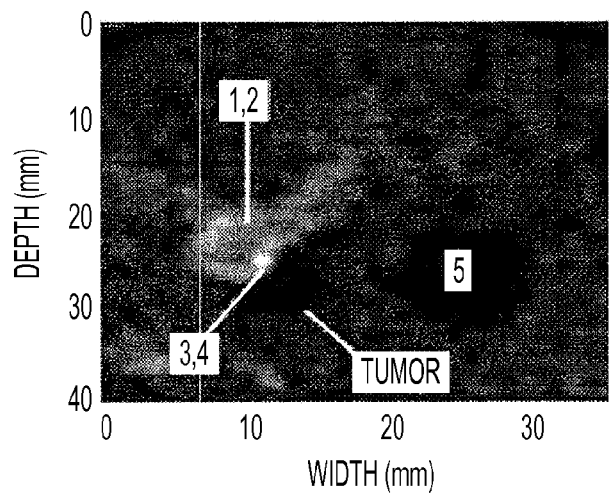
Figure 14G:
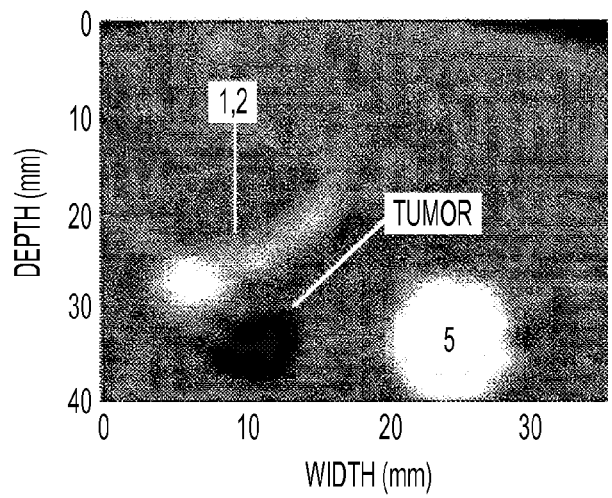
Figure 15A:
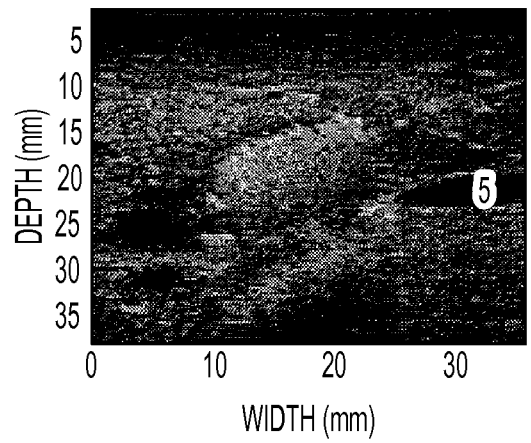
FIGS. 15A-15D show in vivo images of the fourth patient after RF ablation. Similar to FIG. 14, the hepatic vein (marked as 5) can have low strain [as in (15B)] or high strain [as in (15C)] values. (15A) B-mode post-ablation. (15B) Axial strain post-ablation. (15C) Axial strain postablation. (15D) Lateral displacement postablation.
Figure 15B:
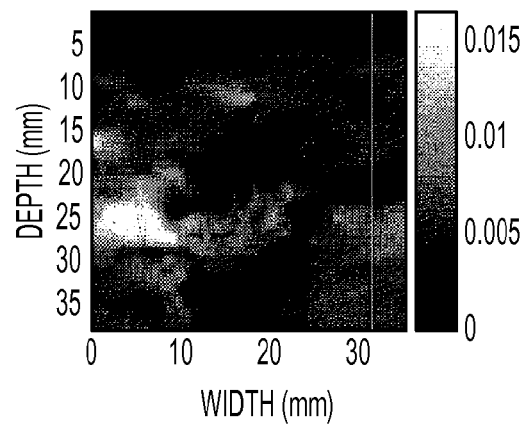
Figure 15C:
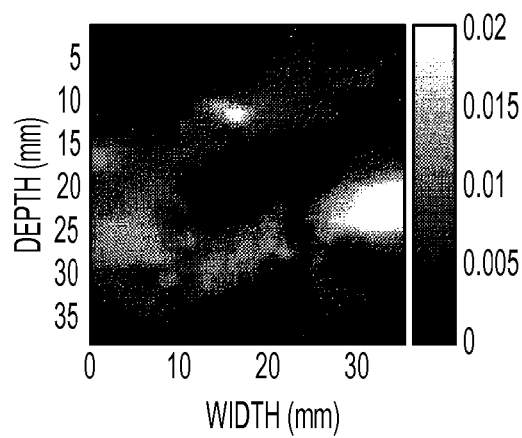
Figure 15D:
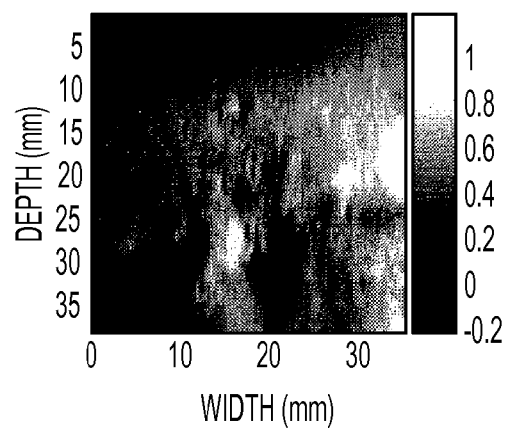

We have also acquired patient RF data of liver ablation prior and after ablation in one of the patient trials. FIG. 14 shows the B-mode, strain and venous and arterial phase[1] CT images obtained before ablation, and FIG. 15 shows the B-mode, strain and lateral displacement images after ablation. (CT scans are performed at different phases after intravenous injection of a contrast agent. In the arterial phase (directly after injection of a contrast agent) arteries will enhance, where as in the venous phase (30-60 s after injection) the hepatic parenchyma and veins will enhance). In FIG. 14, the tumor [marked in the CT images (14F) and (14G)] is not visible in the B-mode image (14A), but is clearly visible in the strain images FIGS. 14B and 14C. While the tissue is getting compressed with the ultrasound probe, the middle hepatic vein (marked as 5) which is only 4-8 cm from vena cava inferior pulsates at high amplitude. The graph in FIG. 14E schematically shows the probe motion and variations in the diameter of the vein. Therefore, the vein can look soft as in (14C) or hard as in (14B) depending on whether its diameter variation is in the same [marked by ellipse 1 in (14E)] or opposite [marked by ellipse 2 in (14E)] direction as the probe motion The effect of pulsation of vessels, a well-known cause of signal decorrelation, is minimized via IRLS resulting in a low noise strain image. In addition, since the 2D AM method gives a dense motion field (same size as RF data), the small artery at the diameter of less than 2 mm [marked as 4 in (14A)] is discernible in (14B) from the low pressure portal vein. The ablated lesion is also discernible in the strain images of FIGS. 15B and (15C). We believe the soft region in the middle of the two hard ablation lesions in FIGS. 15B and 15C and (15C) (at the depth of 25-30 mm and width of 10-25 mm) is not close to any of the 10 tines of the ablation probe. Therefore because of its proximity to veins and vessels its temperature has remained low.

V. Discussion

The resolution of the method is formally studied in Section IV-A using the phantom experiment. Future work will include more intuitive measures for resolution in terms of the smallest detectable target as a function of its elasticity difference with the background.

The cost function is a regularized function of all displacements on an A-line. This makes the methods robust to noise which exist throughout the image. Besides, the AM methods are not window-based and therefore they do not suffer from decorrelation within the window. As a result, both AM methods work for strains as high as 10%. In addition, the IRLS outlier rejection technique makes the AM methods robust to local sources of decorrelation such as out-of-plane motion of movable structures or blood flow.

Global stretching assumes a constant strain across the depth and stretches one of the RF-limes accordingly. It is shown that it enhances the quality of correlation based elastography methods. The reason is that the strain of each point can be assumed to be the global strain (fixed for each RF-line) plus some perturbation, i.e., constant strain is a better approximation than zero strain. Biasing the regularization is motivated by the same reason and involves almost no additional computational cost.

Improvement in the SNR and CNR achieved with Kalman filtering differentiation is due to utilizing the (piecewise) continuity of the strain field. One could think of a unified framework which includes both the 2D AM and the Kalman filtering and directly calculates the strain field. We made an effort to formulate (15) in terms of strain values. Unfortunately, the coefficient matrix in the left-hand side became a full matrix for our desired regularization. Such large full system cannot be solved in real-time.

The least squares differentiation of Section II-D can be incorporated in the Kalman filter. This can be simply done by defining the state at each point to be the displacement and the strain of that point. The observed variables are the noisy displacement measurements from 2D AM. Solving for the state gives a strain estimate at each point. However, we preferred to follow the common approach of first finding the strain by solving least squares. In addition, the axial and lateral displacements can be considered as two channels of a measurement and a Kalman filter that takes into account both intra-channel (spatial) and inter-channel variations can be developed. This is a subject of future work.

Lateral displacement estimation with 2D AM is of order of magnitude less accurate than the axial displacement estimates. We tested the following algorithm for calculating the lateral displacement field based on 1D AM: run 1D AM to find the axial displacement field, then transpose both ultrasound images $T_1$ and $T_2$ and run 1D AM again using A calculated in the previous step. The axial displacement field calculated for the transposed images is in fact the lateral displacement of the original images. Although considerably more computationally expensive than 2D AM, this algorithm did not improve the lateral displacement estimation. Therefore only images of lateral displacement are provided for the patient trials because the lateral strain did not show the ablation lesion. This is in accordance with recent work [36] which only shows the lateral displacement. A 2D displacement field can be utilized to calculate the thermal expansion and to reconstruct the strain tensor. Incorporation of the synthetic lateral phase [61]-[63], into 2D AM to further improve the accuracy of the lateral displacement measurement is also a subject of future work.

In cases where the two ultrasound frames correlate very poorly throughout the image, 1D AM outperforms 2D AM because DP is run for the entire image in 1D AM. However, in those cases the strain images are of very low quality even with 1D AM. In cases where the images correlate reasonably, the 2D AM algorithm slightly outperforms 1D AM in terms of the SNR of the axial strain as shown in FIGS. 3E and 3F. Also, 1D AM and 2D AM are very similar in terms of bias and variance as mentioned in the caption of the FIG. 5. And finally, 2D AM is more than 10 times faster than 1D AM because it eliminates the redundant calculations in the DP step of 1D AM. This is important considering that there are combinatorial many ways of choosing two frames for elastography from a sequence of images. Having a fast algorithm, like 2D AM, makes it plausible to invest time to perform real-time frame selection, an area that we are currently working on [16], [64].

Recent work [65] has attempted to reconstruct elasticity from the displacement field for monitoring thermal ablation. It has also shown that [66] compared to strain images, elasticity images have both higher correlation with the ablation zone and give higher CNR. Another work [67] has utilized the solution of the elasticity reconstruction to improve motion estimation in an iterative framework. Calculation of the elasticity modulus in our ablation monitoring trials is an area of future work.

Statistical analysis of the residuals is a subject of future work. The sum of squared differences used as the similarity metric in our cost function is suitable if ultrasound noise can be modeled as additive Gaussian noise. However, ultrasound noise is not simply additive Gaussian and it has been shown that similarity metrics that model the noise process considering physics of ultrasound give more accurate results [68]. Performance of the 2D AM method for images that are not fully developed speckles (i.e., have few scatterers per resolution cell) is also a subject of future work.

Current implementations of the 1D AM and 2D AM take, respectively, 0.4 s and 0.04 s to generate strain images (axial for 1D AM and axial and lateral for 2D AM) of size 1000×100 on a 3.8 GHz P4 CPU. DP contributes to more than 90% of the running time of the 1D AM, and that's why it is slower than 2D AM where DP is only run for a single A-line. The running time of both methods changes linearly with the size of the image.

VI. Conclusion

Two regularized elastography methods, 1D AM and 2D AM, are introduced for calculating the motion field between two ultrasound images. They both give dense subsample motion fields (1D AM gives subsample axial and integer sample lateral and 2D AM gives subsample axial and lateral) in real-time. The size of the motion fields is the same as the size of the RF-data (except for few samples from the boundary whose displacements are not calculated). Such dense motion fields lead to dense strain fields which are critical in detecting small lesions. The prior of tissue motion continuity is exploited in the AM methods to minimize the effect of signal decorrelation. The regularization term is biased with the average strain in the image to minimize underestimation of the strain values. Parts of the image that have very low correlation are treated as outliers and their effect is minimized via IRLS. The strain image is calculated by differentiating the motion fields using least squares regression and Kalman filtering. The performance of the proposed elastography algorithms is analyzed using Field II and finite element simulations, and phantom experiments. Clinical trials of monitoring RF ablation therapy for liver cancer in four patients are also presented. An implementation of the 2D AM method, the least squares regression and the Kalman filter in MATLAB mex functions, as well as some of the phantom and patient RF data used in this work are available for academic research and can be downloaded (http://www.cs.jhu.edu/~rivaz/UltrasoundElastography).

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the scope of the invention, as appreciated by those skilled in the art in light of the above teachings. It is therefore to be understood that, within the scope of the claims and their equivalents, the invention may be practiced otherwise than as specifically described.

References

[1] K. Parker, L. Taylor, S. Gracewski, and D. Rubens, "A unified view of imaging the elastic properties of tissue," *J. Acoust. Soc. Amer.*, vol. 117, pp. 2705-2712, May 2005.

[2] J. Greenleaf, M. Fatemi, and M. Insana, "Selected methods for imaging elastic properties of biological tissues," *Annu. Rev. Biomed.*, vol. 5, pp. 57-78, April 2003.

[3] J. Ophir, S. Alam, B. Garra, F. Kallel, E. Konofagou, T. Krouskop, and T. Varghese, "Elastography," *Annu. Rev. Biomed. Eng.*, vol. 213, pp. 203-233, November 1999.

[4] L. Gao, K. Parker, R. Lerner, and S. Levinson, "Imaging of the elastic properties of tissue—A review," *Ultrasound Med. Biol.*, vol. 22, no. 8, pp. 959-977, August 1996.

[5] K. Hiltawsky, M. Kruger, C. Starke, L. Heuser, H. Ermert, and A. Jensen, "Freehand ultrasound elastography of breast lesions: Clinical results," *Ultrasound Med. Biol.*, vol. 27, pp. 1461-1469, November 2001.

[6] M. Doyley, J. Bamber, F. Fuechsel, and N. Bush, "A freehand elastographic imaging approach for clinical breast imaging: System development and performance evaluation," *Ultrasound Med. Biol.*, vol. 27, pp. 1347-1357, 2001.

[7] M. Yamakawa, N. Nitta, T. Shiina, T. Matsumura, S. Tamano, T. Mitake, and E. Ueno, "High-speed freehand tissue elasticity imaging for breast diagnosis," *Jpn. J. Appl. Phys.*, vol. 42, no. 5B, pp. 3265-3270, May 2003.

[8] T. Hall, Y. Zhu, and C. Spalding, "In vivo real-time freehand palpation imaging," *Ultrasound Med. Biol.*, vol. 29, pp. 427-435, March 2003.

[9] J. Lindop, G. Treece, A. Gee, and R. Prager, "3D elastography using freehand ultrasound," *Ultrasound Med. Biol.*, vol. 32, pp. 529-545, April 2006.

[10] E. Turgay, S. Salcudean, and R. Rohling, "Identifying the mechanical properties of tissue by ultrasound strain imaging," *Ultrasound Med. Biol.*, vol. 32, no. 2, pp. 221-235, February 2006.

[11] A. Lorenz, H. Sommerfeld, M. Garcia-Schurmann, S. Philippou, T. Senge, and H. Ermert, "A new system for the acquisition of ultrasonic multicompression strain images of the human prostate in vivo," *IEEE Trans. Ultrason. Ferroelectr. Freq. Control*, vol. 46, no. 9, pp. 1147-1154, September 1999.

[12] E. Konofagou, J. D'hooge, and J. Ophir, "Myocardial elastography—A feasibility study in vivo," *Ultrasound Med. Biol.*, vol. 28, no. 4, pp. 475-482, April 2002.

[13] J. Rubin, S. Aglyamov, T. Wakefield, M. ODonnell, and S. Emelianov, "Internal displacement and strain imaging using ultrasound speckle tracking," *IEEE Trans. Ultrason. Ferroelectr. Freq. Control*, vol. 22, pp. 443-448, 2003.

[14] T. Varghese, J. Zagzebski, and F. Lee, "Elastography imaging of thermal lesion in the liver following radio frequency ablation: Preliminary results," *Ultrasound Med. Biol.*, vol. 28, no. 11, pp. 1467-1473, 2002.

[15] H. Rivaz, I. Fleming, L. Assumpcao, G. Fichtinger, U. Hamper, M. Choti, G. Hager, and E. Boctor, "Ablation monitoring with elastography: 2d in-vivo and 3d ex-vivo studies," in *Med. Image Comput. Comput. Assist. Intervent. MICCAI*, New York, September 2008, pp. 458-466.

[16] H. Rivaz, P. Foroughi, I. Fleming, R. Zellars, E. Boctor, and G. Hager, "Tracked regularized ultrasound elastography for targeting breast radiotherapy," in *Med. Image Comput. Computer Assist. Intervent. MICCAI*, London, U.K., September 2009, pp. 507-515.

[17] A. Lyshchik et al., "Thyroid gland tumor diagnosis at US elastography," *Radiology*, vol. 237, no. 1, pp. 202-211, August 2005.

[18] F. Viola and W. Walker, "A comparison of the performance of time-delay estimators in medical ultrasound," *IEEE Trans. Ultrason. Ferroelectr. Freq. Control*, vol. 50, no. 4, pp. 392-401, April 2003.

[19] A. Pesavento, C. Perrey, M. Krueger, and H. Ermert, "A time efficient and accurate strain estimation concept for ultrasonic elastography using iterative phase zero estimation," *IEEE Trans. Ultrason. Ferroelectr. Freq. Control*, vol. 46, pp. 1057-1067, September 1999.

[20] H. Hasegawa and H. Kanai, "Improving accuracy in estimation of artery wall displacement by referring to center frequency of RF echo," *IEEE Trans. Ultrason. Ferroelectr. Freq. Control*, vol. 53, no. 1, pp. 52-63, January 1999.

[21] J. Lindop, G. Treece, A. Gee, and R. Prager, "Phase-based ultrasonic deformation estimation," *IEEE Trans. Ultrason. Ferroelectr. Freq. Control*, vol. 55, no. 1, pp. 94-111, 2008.

[22] W. Walker and G. Trahey, "A fundamental limit on delay estimation using partially correlated speckle signals," *IEEE Trans. Ultrason. Ferroelectr. Freq. Control*, vol. 42, no. 2, pp. 301-308, March 1995.

[23] F. Yeung, S. Levinson, and K. Parker, "Multilevel and motion model-based ultrasonic speckle tracking algorithms," *Ultrasound Med. Biol.*, vol. 24, pp. 427-441, March 1998.

[24] M. O'Donnell, R. Skovoroda, M. Shapo, and S. Emelianov, "Internal displacement and strain imaging using ultrasonic speckle tracking," *IEEE Trans. Ultrason. Ferroelectr. Freq. Control*, vol. 41, no. 3, pp. 314-325, March 1994.

[25] C. Sumi, "Usefulness of ultrasonic strain measurement-based shear modulus reconstruction for diagnosis and thermal treatment," *IEEE Trans. Ultrason. Ferroelectr. Freq. Control*, vol. 52, no. 10, pp. 1670-1689, October 2005.

[26] P. Barbone and J. Bamber, "Quantitative elasticity imaging: What can and cannot be inferred from strain images," *Phys. Med. Biol.*, vol. 47, pp. 2147-2164, June 2002.

[27] C. Sumi, "Reconstructions of shear modulus, Poisson's ratio, and density using approximate mean normal stress lambda epsilon alpha alpha as unknown," *IEEE Trans. Ultrason. Ferroelectr. Freq. Control*, vol. 53, no. 12, pp. 2416-2434, December 2006.

[28] L. Bohs and G. Trahey, "A novel method for angle independent ultrasonic imaging of blood flow and tissue motion," *IEEE Trans. Ultrason. Ferroelectr. Freq. Control*, vol. 38, no. 3, pp. 280-286, March 1991.

[29] P. Chaturvedi, M. Insana, and T. Hall, "2-d companding for noise reduction in strain imaging," *IEEE Trans. Ultrason. Ferroelectr. Freq. Control*, vol. 45, no. 1, pp. 179-191, January 1998.

[30] M. Rao, Q. Chen, H. Shi, T. Varghese, E. Madsen, J. Zagzebski, and T. Wilson, "Normal and shear strain estimation using beam steering on linear-array transducers," *Ultrasound Med. Biol.*, vol. 33, no. 1, pp. 57-66, January 2007.

[31] E. Konofagou and J. Ophir, "A new elastographic method for estimation and imaging of lateral displacements, lateral strains, corrected axial strains and Poisson's ratios in tissues," *Ultrasound Med. Biol.*, vol. 24, no. 8, pp. 1183-1199, 1998.

[32] R. Maurice, J. Ohayon, Y. Fretigny, M. Bertrand, G. Soulez, and G. Cloutier, "Noninvasive vascular elastography: Theoretical framework," *IEEE Trans. Med. Imag.*, vol. 23, no. 2, pp. 164-180, February 2004.

[33] R. Maurice and M. Bertrand, "Lagrangian speckle model and tissue-motion estimation theory," *IEEE Trans. Med. Imag.*, vol. 18, no. 7, pp. 593-603, July 1999.

[34] M. Lubinski, S. Emelianov, K. Raghavan, A. Yagle, A. Skovoroda, and M. O'Donnell, "Lateral displacement estimation using tissue incompressibility," *IEEE Trans. Ultrason. Ferroelectr. Freq. Control*, vol. 43, no. 2, pp. 247-255, March 1996.

[35] C. Pellot-Barakat, F. Frouin, M. Insana, and A. Herment, "Ultrasound elastography based on multiscale estimations of regularized displacement fields," *IEEE Trans. Med. Imag.*, vol. 23, no. 2, pp. 153-163, February 2004.

[36] E. Brusseau, J. Kybic, J. Deprez, and O. Basset, "2-D locally regularized tissue strain estimation from radio-frequency ultrasound images: Theoretical developments and results on experimental data," *IEEE Trans. Med. Imag.*, vol. 27, no. 2, pp. 145-160, February 2008.

[37] C. Sumi, "Regularization of tissue shear modulus reconstruction using strain variance," *IEEE Trans. Ultrason. Ferroelectr. Freq. Control*, vol. 55, no. 2, pp. 297-307, February 2008.

[38] C. Sumi and K. Sato, "Regularization for ultrasonic measurements of tissue displacement vector and strain tensor," *IEEE Trans. Ultrason. Ferroelectr. Freq. Control*, vol. 55, no. 4, pp. 787-799, April 2008.

[39] G. Treece, J. Lindop, A. Gee, and R. Prager, "Uniform precision ultrasound strain imaging," *IEEE Trans. Ultrason. Ferroelectr. Freq. Control*, vol. 56, no. 11, pp. 2420-2436, November 2009.

[40] H. Rivaz, E. Boctor, P. Foroughi, G. Fichtinger, and G. Hager, "Ultrasound elastography: A dynamic programming approach," *IEEE Trans. Med. Imag.*, vol. 27, no. 10, pp. 1373-1377, October 2008.

[41] G. Welch and G. Bishop, An introduction to the Kalman filter Univ. North Carolina, Chapel Hill, TR 95-041, 1995.

[42] A. Amini, T. Weymouth, and R. Jain, "Using dynamic programming for solving variational problems in vision," *IEEE Trans. Pattern Anal. Mach. Intell.*, vol. 12, no. 9, pp. 855-867, September 1990.

[43] P. Huber, *Robust Statistics*. New York: Wiley.

[44] G. Hager and P. Belhumeur, "Efficient region tracking with parametric models of geometry and illumination," *IEEE Trans. Pattern Anal. Mach. Intell.*, vol. 20, no. 10, pp. 1025-1039, October 1998.

[45] P. Holland and R. Welsch, "Robust regression using iteratively reweighted least squares," *Commun. Statist. Theory Methods*, vol. A6, pp. 813-827, 1977.

[46] L. Sandrin, M. Tanter, S. Catheline, and M. Fink, "Shear modulus imaging with 2-D transient elastography," *IEEE Trans. Ultrason. Ferroelectr. Freq. Control*, vol. 49, no. 4, pp. 426-435, April 2002.

[47] M. Tanter, J. Bercoff, L. Sandrin, and M. Fink, "Ultrafast compound imaging for 2-d motion vector estimation: Application to transient elastography," *IEEE Trans. Ultrason. Ferroelectr. Freq. Control*, vol. 49, no. 10, pp. 1363-1374, October 2002.

[48] L. Chen, G. Treece, J. Lindop, A. Gee, and R. Prager, "A quality-guided displacement tracking algorithm for ultrasonic elasticity imaging," *Med. Imag. Anal.*, vol. 13, no. 2, pp. 286-296, April 2009.

[49] J. Prince and J. Links, *Medical Imaging Signals and Systems*. Upper Saddle River, N.J.: Prentice Hall, 2006.

[50] H. Shum and R. Szeliski, "Construction of panoramic mosaics with global and local alignment," *Int. J. Comput. Vis.*, vol. 36, no. 2, pp. 101-130, 2000.

[51] S. Baker and I. Matthews, "Lucas-kanade 20 years on: A unifying framework," *Int. J. Comput. Vis.*, vol. 56, no. 3, pp. 221-255, February 2004.

[52] R. Dugad and N. Ahuja, "Video denoising by combining Kalman and Wiener estimates," in *Int. Conf Image Process. ICIP*, 1999, vol. 4, pp. 152-156.

[53] A. Jensen, "Field: A program for simulating ultrasound systems," *Med. Biol. Eng. Comput.*, vol. 34, pp. 351-353, 1996.

[54] R. Wagner, S. Smith, J. Sandrik, and H. Lopez, "Statistics of speckle in ultrasound B-Scans," *IEEE Trans. Sonics Ultrasonics*, vol. 17, no. 3, pp. 251-268, May 1983.

[55] H. Rivaz, E. Boctor, and G. Fichtinger, "Ultrasound speckle detection using low order moments," in *IEEE Int. Ultrason. Symp.*, October 2006, pp. 2092-2095.

[56] D. Bertsimas and J. Tsitsiklis, *Biomechanics: Mechanical Properties of Living Tissues*. New York: Springer-Verlag, 1993.
[57] T. Krouskop, T. Wheeler, F. Kallel, B. Gana, and T. Hall, "The elastic moduli of breast and prostate tissues under compression," *Ultrason. Imag.*, vol. 20, pp. 260-274, 1998.
[58] J. Liu, K. Abbey, and M. Insana, "Linear approach to axial resolution in elasticity imaging," *IEEE Trans. Ultrason. Ferroelectr. Freq. Control*, vol. 51, no. 6, pp. 716-725, June 2004.
[59] R. Padgett and C. Korte, "Assessment of the effects of pixel loss on image quality in direct digital radiography," *Phys. Med. Biol.*, vol. 49, no. 6, pp. 977-986, March 2004.
[60] M. Doyley, Q. Feng, J. Weaver, and K. Paulsen, "Performance analysis of steady-state harmonic elastography," *Phys. Med. Biol.*, vol. 52, no. 10, pp. 2657-2674, May 2007.
[61] X. Chen, M. Zohdy, S. Emelianov, and M. O'Donnell, "Lateral speckle tracking using synthetic lateral phase," *IEEE Trans. Ultrason. Ferroelectr. Freq. Control*, vol. 51, no. 5, pp. 540-550, May 2004.
[62] E. Ebbini, "Phase-coupled two-dimensional speckle tracking algorithm," *IEEE Trans. Ultrason. Ferroelectr. Freq. Control*, vol. 53, no. 5, pp. 972-990, May 2006.
[63] C. Sumi, "Displacement vector measurement using instantaneous ultrasound signal phase—Multidimensional autocorrelation and Doppler methods," *IEEE Trans. Ultrason. Ferroelectr. Freq. Control*, vol. 55, no. 1, pp. 24-43, January 2008.
[64] P. Foroughi, H. Rivaz, I. Fleming, G. Hager, and E. Boctor, "Tracked ultrasound elastography (true)," *Med. Image Computing Computer Assist. Intervent.*, to be published.
[65] J. Jiang, T. Varghese, E. M. C. Brace, T. Hall, S. Bharat, M. Hobson, J. Zagzebski, and F. Lee, "Youngs modulus reconstruction for radio frequency ablation electrode-induced displacement fields: A feasibility study," *IEEE Trans. Med. Imag.*, vol. 28, pp. 1325-1334, August 2009.
[66] J. Jiang, C. Brace, A. Andreano, R. DeWall, N. Rubert, T. Pavan, T. Fisher, T. Varghese, F. Lee, and T. Hall, "Ultrasound-based relative elastic modulus imaging for visualizing thermal ablation zones in a porcine model," *Phys. Med. Biol.*, vol. 55, pp. 2281-2306, 2010.
[67] M. Miga, "A new approach to elastography using mutual information and finite elements," *Phys. Med. Biol.*, vol. 48, pp. 467-480, 2003.
[68] M. Insana, L. Cook, M. Bilgen, P. Chaturvedi, and Y. Zhu, "Maximum-liklihood approach to strain imaging using ultrasound," *IEEE Trans. Ultrason. Ferroelectr. Freq. Control*, vol. 107, no. 3, pp. 1421-1434, 2000.

We claim:

1. A method of processing ultrasound data, comprising:
receiving ultrasound data for a first ultrasound image, said first ultrasound image being represented as a first set of discrete pixels corresponding to positions of a region of interest;
receiving ultrasound data for a second ultrasound image, said second ultrasound image being represented as a second set of discrete pixels corresponding to positions of said region of interest;
generating a displacement map by minimizing a cost function using a dynamic programming procedure that identifies each of said first set of discrete pixels with a corresponding one of said second set of discrete pixels;
refining said displacement map to obtain intermediate displacement values corresponding to positions between said discrete pixels based on minimizing a local approximation to said cost function;
calculating a physical property of said region of interest based on said displacement map;
wherein said receiving ultrasound data for said first ultrasound image corresponds to said region of interest having a first temperature distribution,
wherein said receiving ultrasound data for said second ultrasound image corresponds to said region of interest having a second temperature distribution, and
said calculating said physical property of said region of interest based on said displacement map is calculating a temperature map.

2. A method of processing ultrasound data according to claim 1, wherein said minimizing said local approximation to said cost function is performed analytically to optimize said intermediate displacement values corresponding to positions within a continuous range between said discrete pixels.

3. A method of processing ultrasound data according to claim 1, wherein said receiving ultrasound data for said first ultrasound image corresponds to said region of interest being under a first compression state,
wherein said receiving ultrasound data for said second ultrasound image corresponds to said region of interest being under a second compression state, and
said calculating said physical property of said region of interest based on said displacement map is calculating a strain map.

4. A method of processing ultrasound data according to claim 3, wherein said calculating said strain map comprises Kalman filtering.

5. A method of processing ultrasound data according to claim 4, further comprising rendering an ultrasound image taking into account said strain map.

6. A method of processing ultrasound data according to claim 1, further comprising rendering an ultrasound image taking into account said temperature map.

7. A method of processing ultrasound data according to claim 1, wherein said cost function is modified to reduce errors on said generating said displacement map due to portions of said region of interest moving out of an imaging plane of at least one of said first and second ultrasound image.

8. A method of processing ultrasound data according to claim 1, wherein said cost function is modified to reduce errors on said generating said displacement map using an iterated reweighted least squares procedure to treat uncorrelated ultrasound data as outliers.

9. A non-transitory computer readable medium comprising software, which software when executed by a computer, causes the computer to:
receive ultrasound data for a first ultrasound image, said first ultrasound image being represented as a first set of discrete pixels corresponding to positions of a region of interest;
receive ultrasound data for a second ultrasound image, said second ultrasound image being represented as a second set of discrete pixels corresponding to positions of said region of interest;
generate a displacement map by minimizing a cost function using a dynamic programming procedure that identifies each of said first set of discrete pixels with a corresponding one of said second set of discrete pixels;
refine said displacement map to obtain intermediate displacement values corresponding to positions between said discrete pixels based on minimizing a local approximation to said cost function;

calculate a physical property of said region of interest based on said displacement map;

wherein said receiving ultrasound data for said first ultrasound image corresponds to said region of interest having a first temperature distribution, wherein said receiving ultrasound data for said second ultrasound image corresponds to said region of interest having a second temperature distribution, and said calculating said physical property of said region of interest based on said displacement map is calculating a temperature map.

10. A non-transitory computer readable medium according to claim 9, wherein said minimizing said local approximation to said cost function is performed analytically to optimize said intermediate displacement values corresponding to positions within a continuous range between said discrete pixels.

11. A non-transitory computer readable medium according to claim 9, wherein said receiving ultrasound data for said first ultrasound image corresponds to said region of interest being under a first compression state, wherein said receiving ultrasound data for said second ultrasound image corresponds to said region of interest being under a second compression state, and said calculating said physical property of said region of interest based on said displacement map is calculating a strain map.

12. A non-transitory computer readable medium according to claim 11, wherein said calculating said strain map comprises Kalman filtering.

13. A non-transitory computer readable medium according to claim 12, wherein said software when executed by said computer, further causes the computer to render an ultrasound image taking into account said strain map.

14. A non-transitory computer readable medium according to claim 9, wherein said software when executed by said computer, further causes the computer to render an ultrasound image taking into account said temperature map.

15. A non-transitory computer readable medium according to claim 9, wherein said cost function is modified to reduce errors on said generating said displacement map due to portions of said region of interest moving out of an imaging plane of at least one of said first and second ultrasound image.

16. A non-transitory computer readable medium according to claim 9, wherein said cost function is modified to reduce errors on said generating said displacement map using an iterated reweighted least squares procedure to treat uncorrelated ultrasound data as outliers.

17. An ultrasound system, comprising:
an ultrasound transducer configured to transmit and receive ultrasound signals;
a data processor arranged to communicate with said ultrasound transducer to receive ultrasound data from said ultrasound transducer,
wherein said data processor is configured to:
receive ultrasound data for a first ultrasound image, said first ultrasound image being represented as a first set of discrete pixels corresponding to positions of a region of interest;
receive ultrasound data for a second ultrasound image, said second ultrasound image being represented as a second set of discrete pixels corresponding to positions of said region of interest;
generate a displacement map by minimizing a cost function using a dynamic programming procedure that identifies each of said first set of discrete pixels with a corresponding one of said second set of discrete pixels;
refine said displacement map to obtain intermediate displacement values corresponding to positions between said discrete pixels based on minimizing a local approximation to said cost function;
calculate a physical property of said region of interest based on said displacement map,
wherein said receiving ultrasound data for said first ultrasound image corresponds to said region of interest having a first temperature distribution;
wherein said receiving ultrasound data for said second ultrasound image corresponds to said region of interest having a second temperature distribution; and
said calculating said physical property of said region of interest based on said displacement map is calculating a temperature map.

18. An ultrasound system according to claim 17, wherein said minimizing said local approximation to said cost function is performed analytically to optimize said intermediate displacement values corresponding to positions within a continuous range between said discrete pixels.

19. An ultrasound system according to claim 17, wherein said receiving ultrasound data for said first ultrasound image corresponds to said region of interest being under a first compression state,
wherein said receiving ultrasound data for said second ultrasound image corresponds to said region of interest being under a second compression state, and
said calculating said physical property of said region of interest based on said displacement map is calculating a strain map.

20. An ultrasound system according to claim 19, wherein said calculating said strain map comprises Kalman filtering.

21. An ultrasound system according to claim 20, wherein said data processor is further configured to render an ultrasound image taking into account said strain map.

22. An ultrasound system according to claim 17, wherein said data processor is further configured to render an ultrasound image taking into account said temperature map.

23. An ultrasound system according to claim 17, wherein said cost function is modified to reduce errors on said generating said displacement map due to portions of said region of interest moving out of an imaging plane of at least one of said first and second ultrasound image.

24. An ultrasound system according to claim 17, wherein said cost function is modified to reduce errors on said generating said displacement map using an iterated reweighted least squares procedure to treat uncorrelated ultrasound data as outliers.

* * * * *